(12) United States Patent
Khleif et al.

(10) Patent No.: US 12,209,127 B2
(45) Date of Patent: *Jan. 28, 2025

(54) ANTIBODIES TO PROGRAMMED CELL DEATH PROTEIN 1

(71) Applicant: Augusta University Research Institute, Inc., Augusta, GA (US)

(72) Inventors: Samir Khleif, Silver Spring, MD (US); Mikayel Mkrtichyan, Tujunga, CA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/473,002

(22) Filed: Sep. 22, 2023

(65) Prior Publication Data

US 2024/0076379 A1  Mar. 7, 2024

Related U.S. Application Data

(63) Continuation of application No. 17/210,117, filed on Mar. 23, 2021, now Pat. No. 11,780,921, which is a continuation of application No. 16/645,289, filed as application No. PCT/US2018/049854 on Sep. 7, 2018, now Pat. No. 11,021,540.

(60) Provisional application No. 62/657,323, filed on Apr. 13, 2018, provisional application No. 62/624,843, filed on Feb. 1, 2018, provisional application No. 62/555,156, filed on Sep. 7, 2017.

(51) Int. Cl.
*C07K 16/28* (2006.01)
*A61K 39/00* (2006.01)
*A61P 35/00* (2006.01)

(52) U.S. Cl.
CPC .......... *C07K 16/2818* (2013.01); *A61P 35/00* (2018.01); *A61K 2039/505* (2013.01); *C07K 2317/34* (2013.01); *C07K 2317/565* (2013.01); *C07K 2317/75* (2013.01); *C07K 2317/92* (2013.01)

(58) Field of Classification Search
CPC ............ C07K 16/2818; C07K 2317/34; C07K 2317/565; C07K 2317/75; C07K 2317/92; A61P 35/00; A61K 2039/505
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,816,397 A | 3/1989 | Boss et al. |
| 4,816,567 A | 3/1989 | Cabilly et al. |
| 5,013,556 A | 5/1991 | Woodle et al. |
| 5,190,929 A | 3/1993 | Borch et al. |
| 5,225,539 A | 7/1993 | Winter |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,766,886 A | 6/1998 | Studnicka et al. |
| 5,807,715 A | 9/1998 | Morrison et al. |
| 5,814,318 A | 9/1998 | Lonberg et al. |
| 5,916,771 A | 6/1999 | Hori et al. |

(Continued)

FOREIGN PATENT DOCUMENTS

| | | |
|---|---|---|
| AU | 2018330180 A1 | 3/2020 |
| BR | 112020004458 A2 | 10/2020 |

(Continued)

OTHER PUBLICATIONS

Abuchowski, et al., Soluble Polymer-Enzyme Adducts, "Enzymes as Drugs" by Hocenberg and Roberts, Chapter 13, Published by Wiley-Interscience, 1981, pp. 367-383.

Angal, et al., A single amino acid substitution abolishes the heterogeneity of chimeric Mouse/human (IgG4) antibody, Mol Immunol., vol. 30, No. 1, Jan. 1993, pp. 105-108.

(Continued)

*Primary Examiner* — Amy E Juedes
*Assistant Examiner* — Peter Johansen
(74) *Attorney, Agent, or Firm* — PABST PATENT GROUP LLP

(57) ABSTRACT

Antibodies and antigen binding fragments thereof are provided that immunospecifically bind to PD-1 and induce or promote an immune response that activates immune cell proliferation or activity. Contrary to the existing paradigm that PD-1 exclusively promotes a suppressive immune response, the disclosed antibodies and antigen binding fragments thereof, immunospecifically bind to PD-1 and cause an activating signal to be delivered to the immune cell that activates the immune cell rather than suppressing the immune cell. In one embodiment, the disclosed antibodies and antigen binding fragments thereof specifically bind to PD-1 expressed on immune cells. The binding of the disclosed antibodies and antigen binding fragments thereof to PD-1 on immune cells causes an activating signal to be transmitted into the immune cell, for example a signal that enhances or promotes cytokine production and/or activation of immune cell proliferation.

21 Claims, 14 Drawing Sheets

Specification includes a Sequence Listing.

(56) References Cited

U.S. PATENT DOCUMENTS

| | | |
|---|---|---|
| 5,939,598 A | 8/1999 | Kucherlapati et al. |
| 6,005,079 A | 12/1999 | Casterman et al. |
| 6,180,370 B1 | 1/2001 | Queen et al. |
| 6,194,551 B1 | 2/2001 | Idusogie et al. |
| 6,311,415 B1 | 11/2001 | Lind |
| 6,350,861 B1 | 2/2002 | Co et al. |
| 6,407,213 B1 | 6/2002 | Carter et al. |
| 7,052,694 B2 | 5/2006 | Pease et al. |
| 7,332,582 B2 | 2/2008 | Hardy et al. |
| 7,390,888 B2 | 6/2008 | Pease et al. |
| 7,411,051 B2 | 8/2008 | Rosen et al. |
| 7,488,802 B2 | 2/2009 | Collins et al. |
| 7,521,051 B2 | 4/2009 | Collins et al. |
| 7,524,498 B2 | 4/2009 | Hardy et al. |
| 7,563,869 B2 | 7/2009 | Honjo et al. |
| 7,795,494 B2 | 9/2010 | Ghayur |
| 7,981,416 B2 | 7/2011 | Hardy et al. |
| 8,043,620 B2 | 10/2011 | Qian et al. |
| 8,088,905 B2 | 1/2012 | Collins et al. |
| 8,114,845 B2 | 2/2012 | Langermann et al. |
| 8,188,238 B2 | 5/2012 | Pease et al. |
| 8,232,449 B2 | 7/2012 | Tanamachi et al. |
| 8,287,856 B2 | 10/2012 | Li et al. |
| 8,383,796 B2 | 2/2013 | Korman et al. |
| 8,481,687 B2 | 7/2013 | Vincent et al. |
| 8,552,154 B2 | 10/2013 | Freeman et al. |
| 8,580,247 B2 | 11/2013 | Li et al. |
| 8,609,089 B2 | 12/2013 | Langermann et al. |
| 8,703,485 B2 | 4/2014 | Buelow |
| 8,709,416 B2 | 4/2014 | Langermann et al. |
| 8,728,474 B2 | 5/2014 | Honjo et al. |
| 8,779,105 B2 | 7/2014 | Korman et al. |
| 8,835,712 B2 | 9/2014 | Tomizuka et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,109,025 B2 | 8/2015 | Gurney et al. |
| 9,127,071 B2 | 9/2015 | Yoshida et al. |
| 9,205,148 B2 | 12/2015 | Langermann et al. |
| 9,255,147 B2 | 2/2016 | Pease et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,388,446 B2 | 7/2016 | Murphy et al. |
| 9,393,301 B2 | 7/2016 | Honjo et al. |
| 9,445,581 B2 | 9/2016 | Bradley et al. |
| 9,492,539 B2 | 11/2016 | Korman et al. |
| 9,492,540 B2 | 11/2016 | Korman et al. |
| 9,499,838 B2 | 11/2016 | Kuroiwa et al. |
| 9,580,507 B2 | 2/2017 | Korman et al. |
| 9,686,970 B2 | 6/2017 | MacDonald et al. |
| 9,708,635 B2 | 7/2017 | Murphy et al. |
| 9,987,500 B2 | 6/2018 | Papadopoulos et al. |
| 10,155,037 B2 | 12/2018 | Abdiche et al. |
| 10,428,146 B2 | 10/2019 | Qiu et al. |
| 10,897,541 B2 | 1/2021 | Christiano et al. |
| 11,021,540 B2 | 6/2021 | Khleif et al. |
| 11,780,921 B2 | 10/2023 | Khleif et al. |
| 2003/0229208 A1 | 12/2003 | Queen et al. |
| 2004/0049014 A1 | 3/2004 | Queen et al. |
| 2005/0037000 A1 | 2/2005 | Stavenhagen et al. |
| 2005/0064514 A1 | 3/2005 | Stavenhagen et al. |
| 2006/0088883 A1 | 4/2006 | Smider |
| 2007/0202077 A1 | 8/2007 | Brodsky et al. |
| 2009/0130114 A1 | 5/2009 | Qian et al. |
| 2009/0217401 A1 | 8/2009 | Korman et al. |
| 2010/0074916 A1 | 3/2010 | Nabel et al. |
| 2011/0256154 A1 | 10/2011 | Vincent et al. |
| 2012/0251556 A1 | 10/2012 | Allison et al. |
| 2013/0273089 A1 | 10/2013 | Getts et al. |
| 2013/0309250 A1 | 11/2013 | Cogswell et al. |
| 2014/0271629 A1 | 9/2014 | Corbit et al. |
| 2015/0203579 A1 | 7/2015 | Papadopoulos et al. |
| 2015/0210769 A1* | 7/2015 | Freeman ................ A61P 37/02 435/254.2 |
| 2016/0032019 A1 | 2/2016 | Xiao |
| 2016/0159905 A1 | 6/2016 | Abdiche et al. |
| 2017/0210821 A1 | 7/2017 | Zimring |
| 2017/0239351 A1 | 8/2017 | Hamdy et al. |
| 2017/0240644 A1 | 8/2017 | Zhou et al. |
| 2020/0317808 A1 | 10/2020 | Afar |
| 2021/0032341 A1 | 2/2021 | Khleif et al. |

FOREIGN PATENT DOCUMENTS

| | | |
|---|---|---|
| CA | 3074647 A1 | 3/2019 |
| CL | 2020000576 A1 | 12/2020 |
| CN | 1753912 A | 3/2006 |
| CN | 101213297 A | 7/2008 |
| CN | 111133005 A | 5/2020 |
| CO | 2020003165 A2 | 5/2020 |
| EP | 0239400 A2 | 9/1987 |
| EP | 0519596 A1 | 12/1992 |
| EP | 0592106 A1 | 4/1994 |
| EP | 2530091 A1 | 12/2012 |
| EP | 3679070 A1 | 7/2020 |
| IL | 272911 A | 4/2020 |
| JP | 2011504501 A | 2/2011 |
| JP | 2013523166 A | 6/2013 |
| JP | 2014524746 A | 9/2014 |
| JP | 2015504419 A | 2/2015 |
| JP | 2016531304 A | 10/2016 |
| JP | 2020532991 A | 11/2020 |
| KR | 20200045520 A | 5/2020 |
| RU | 2014111999 A | 3/2016 |
| WO | 9109967 A1 | 7/1991 |
| WO | 9110741 A1 | 7/1991 |
| WO | 9317105 A1 | 9/1993 |
| WO | 9404678 A1 | 3/1994 |
| WO | 9425591 A1 | 11/1994 |
| WO | 9633735 A1 | 10/1996 |
| WO | 9634096 A1 | 10/1996 |
| WO | 9816654 A1 | 4/1998 |
| WO | 9824893 A2 | 6/1998 |
| WO | 9846645 A2 | 10/1998 |
| WO | 9850433 A2 | 11/1998 |
| WO | 9958572 A1 | 11/1999 |
| WO | 2007056539 A2 | 5/2007 |
| WO | 2008112017 A2 | 9/2008 |
| WO | 2010036959 A2 | 4/2010 |
| WO | 2011110621 A1 | 9/2011 |
| WO | 2013012747 A1 | 1/2013 |
| WO | 2015112800 A1 | 7/2015 |
| WO | 2015112900 A1 | 7/2015 |
| WO | 2016014688 A2 | 1/2016 |
| WO | 2016020856 A2 | 2/2016 |
| WO | 2016168716 A1 | 10/2016 |
| WO | 2019051164 A1 | 3/2019 |

OTHER PUBLICATIONS

Ausubel, et al., Mutagenesis of Cloned DNA, Short Protocols in Molecular Biology, Chapter 8, Published by Green Publishing Associates and John Wiley & Sons, 1992, pp. 8-1-8-25.

Baca, et al., Antibody humanization using monovalent phage display, J Biol Chem., vol. 272, No. 16, Apr. 18, 1997, pp. 10678-10684.

Bass, et al., Immunopotentiation with low-dose cyclophosphamide in the active specific immunotherapy of cancer, Cancer Immunol Immunother., vol. 47, No. 1, Sep. 1998, pp. 1-12.

Berger, et al., Phase I safety and pharmacokinetic study of CT-011, a humanized antibody interacting with PD-1, in patients with advanced hematologic malignancies, Clin Cancer Res., vol. 14, No. 10, May 15, 2008, pp. 3044-3051.

Brode, et al., Immune-potentiating effects of the chemotherapeutic drug cyclophosphamide, Crit Rev Immunol., vol. 28, No. 2, 2008, pp. 109-126.

Bruggemann, et al., Human antibody production in transgenic animals, Arch Immunol Ther Exp (Warsz)., vol. 63, No. 2, Apr. 2015, pp. 101-108.

(56) References Cited

OTHER PUBLICATIONS

Butte, et al., Programmed death-1 ligand 1 interacts specifically with the B7-1 costimulatory molecule to inhibit T cell responses, Immunity., vol. 27, No. 1, Jul. 2007, pp. 111-122.

Caldas, et al., Design and synthesis of germline-based hemi-humanized single-chain Fv against the CD18 surface antigen, Protein Eng., vol. 13, No. 5, May 2000, pp. 353-360.

Chothia, et al., Canonical structures for the hypervariable regions of immunoglobulins, J Mol Biol., vol. 196, No. 4, Aug. 20, 1987, pp. 901-917.

Chothia, et al., Structural determinants in the sequences of immunoglobulin variable domain, J Mol Biol., vol. 278, No. 2, May 1, 1988, pp. 457-479.

Chilean Examiner's Report, received in CL 2020-000576, received on Dec. 11, 2021, 15 pages (1 page of English Translation and 14 Pages Official Copy).

Couto, et al., Anti-BA46 monoclonal antibody Mc3: humanization using a novel positional consensus and in vivo and in vitro characterization, Cancer Res., vol. 55, No. 8, Apr. 15, 1995, pp. 1717-1722.

Couto, et al., Designing human consensus antibodies with minimal positional templates, Cancer Res., vol. 55, No. 23 Suppl, Dec. 1, 1995, pp. 5973s-5977s.

Cubillos-Ruiz, et al., Polyethylenimine-based siRNA nanocomplexes reprogram tumor-associated dendritic cells via TLR5 to elicit therapeutic antitumor immunity, J Clin Invest., vol. 119, No. 8, Aug. 2009, pp. 2231-2244.

Erbe, et al., Small molecule ligands define a binding site on the immune regulatory protein B7.1, J Biol Chem., vol. 277, No. 9, Mar. 1, 2002, pp. 7363-7368.

Freeman, Gordon J., Structures of PD-1 with its ligands: sideways and dancing cheek to cheek, Proc Natl Acad Sci U S A., vol. 105, No. 30, Jul. 29, 2008, pp. 10275-10276.

Gillies, et al., High-level expression of chimeric antibodies using adapted cDNA variable region cassettes, J Immunol Methods., vol. 125, No. 1-2, Dec. 20, 1989, pp. 191-202.

Grimaldi, et al., Nivolumab plus interferon-γ in the treatment of intractable mucormycosis, Lancet Infect Dis., vol. 17, No. 1, Jan. 2017, p. 18.

Guatelli, et al., Isothermal, in vitro amplification of nucleic acids by a multienzyme reaction modeled after retroviral replication, Proc Natl Acad Sci U S A., vol. 87, No. 5, Mar. 1990, pp. 1874-1878.

He, et al., Development of PD-1/PD-L1 Pathway in Tumor Immune Microenvironment and Treatment for Non-Small Cell Lung Cancer, Sci Rep., vol. 5, No. 13110, Aug. 17, 2015, 9 pages.

Hengst, et al., Cooperation between cyclophosphamide tumoricidal activity and host antitumor immunity in the cure of mice bearing large MOPC-315 tumors, Cancer Res., vol. 41, No. 6, Jun. 1981, pp. 2163-2167.

Hengst, et al., Importance of timing in cyclophosphamide therapy of MOPC-315 tumor-bearing mice, Cancer Res., vol. 40, No. 7, Jul. 1, 1980, pp. 2135-2141.

International Preliminary Report on Patentability received for PCT Patent Application No. PCT/US18/049854, mailed on Mar. 19, 2020, 10 pages.

International Search Report received for PCT Patent Application No. PCT/US2018/049854, mailed on Dec. 10, 2018, 9 pages.

Iwai, et al., Cancer immunotherapies targeting the PD-1 signaling pathway, J Biomed Sci., vol. 24, No. 1, Apr. 4, 2017, 11 pages.

Jakobovits, Aya, Production of fully human antibodies by transgenic mice, Curr Opin Biotechnol., vol. 6, No. 5, Oct. 1995, pp. 561-566.

Jakobovits, et al., From XenoMouse technology to panitumumab, the first fully human antibody product from transgenic mice, Nat Biotechnol., vol. 25, No. 10, Oct. 2007, pp. 1134-1143.

Jasion, et al., Survival and digestibility of orally-administered immunoglobulin. Preparations containing IgG through the gastrointestinal tract in humans, Nutr J., vol. 14, No. 22, Mar. 7, 2015, 8 pages.

Jones, et al., Replacing the complementarity-determining regions in a human antibody with those from a mouse, Nature., vol. 321, No. 6069, 1986, pp. 522-525.

Lazar-Molnar, et al., Crystal structure of the complex between programmed death-1 (PD-1) and its ligand PD-L2, Proc Natl Acad Sci U S A., vol. 105, No. 30, Jul. 29, 2008, pp. 10483-10488.

Li, et al., Vascular endothelial growth factor blockade reduces intratumoral regulatory T cells and enhances the efficacy of a GM-CSF-secreting cancer immunotherapy, Clin Cancer Res., vol. 12, No. 22, Nov. 15, 2006, pp. 6808-6816.

Liang, et al., Design of new oxazaphosphorine anticancer drugs, Curr Pharm Des., vol. 13, No. 9, 2007, pp. 963-978.

Lonberg, et al., Human antibodies from transgenic mice, Int Rev Immunol., vol. 13, No. 1, 1995, pp. 65-93.

Lonberg, Nils, Human antibodies from transgenic animals, Nat Biotechnol., vol. 23, No. 9, Sep. 2005, pp. 1117-1125.

Machiels, et al., Cyclophosphamide, doxorubicin, and paclitaxel enhance the antitumor immune response of granulocyte/macrophage-colony stimulating factor-secreting whole-cell vaccines in HER-2/neu tolerized mice, Cancer Res., vol. 61, No. 9, May 1, 2001, pp. 3689-3697.

Mathiowitz, et al., Novel Microcapsules for delivery systems, Reactive Polymers, vol. 6, Oct. 1987, pp. 275-283.

Mathiowitz, et al., Polyanhydride microspheres as drug carriers I. Hot-melt microencapsulation, Journal of Controlled Release, vol. 5, No. 1, Jun. 1987, pp. 13-22.

Mathiowitz, et al., Polyanhydride microspheres as drug carriers. II. Microencapsulation by solvent removal, Journal of Applied Polymer Science, vol. 35, No. 3, Feb. 20, 1988, pp. 755-774.

Morea, et al., Antibody modeling: implications for engineering and design, Methods., vol. 20, No. 3, Mar. 2000, pp. 267-279.

Morrison, S L., Transfectomas provide novel chimeric antibodies, Science, vol. 229, No. 4719, Sep. 20, 1985, pp. 1202-1207.

Most, et al., Tumor eradication after cyclophosphamide depends on concurrent depletion of regulatory T cells: a role for cycling TNFR2-expressing effector-suppressor T cells in limiting effective chemotherapy, Cancer Immunol Immunother., vol. 58, No. 8, Aug. 2009, pp. 1219-1228.

Muyldermans, et al., Recognition of antigens by single-domain antibody fragments: The superfluous luxury of paired domains, Trends Biochem Sci., vol. 26, No. 4, Apr. 2001, pp. 230-235.

Notice of Allowance received for U.S. Appl. No. 16/645,289, mailed on Dec. 22, 2020.

Office Action received for European Patent Application No. 18779878.0, mailed on Aug. 20, 2021, 5 pages.

Office Action received in NC2020/0003165, issued on Jan. 14, 2022, 17 pages (8 pages of English Translation and 9 pages of Official Copy).

Padlan, Eduardo A., A possible procedure for reducing the immunogenicity of antibody variable domains while preserving their ligand-binding properties, Mol Immunol., vol. 28, No. 4-5, 1991, pp. 489-498.

Pedersen, et al., Comparison of surface accessible residues in human and murine immunoglobulin Fv domains. Implication for humanization of murine antibodies, J Mol Biol., vol. 235, No. 3, Jan. 21, 1994, pp. 959-973.

Philippart, et al., Oral Delivery of Therapeutic Proteins and Peptides: An Overview of Current Technologies and Recommendations for Bridging from Approved Intravenous or Subcutaneous Administration to Novel Oral Regimens, Drug Res (Stuttg)., vol. 66, No. 3, Mar. 2016, pp. 113-120.

Pluckthun, A., Antibodies from *Escherichia coli*, "The Pharmacology of Monoclonal Antibodies" by Rosenburg and Moore, vol. 113, Chapter 11, Published by Springer-Verlag, 1994, pp. 269-315.

Presta, Leonard G., Antibody engineering, Current Opinion in Structural Biology., vol. 2, No. 4, Aug. 1992, pp. 593-596.

Reilly, et al., Oral delivery of antibodies. Future pharmacokinetic trends, Clin Pharmacokinet., vol. 32, No. 4, Apr. 1997, pp. 313-323.

Riechmann, et al., Reshaping human antibodies for therapy, Nature., vol. 332, No. 6162, Mar. 24, 1988, pp. 323-327.

Riechmann, et al., Single domain antibodies: comparison of camel VH and camelised human VH domains, J Immunol Methods, vol. 231, No. 1-2, Dec. 10, 1999, pp. 25-28.

(56) References Cited

OTHER PUBLICATIONS

Riley, James L., PD-1 signaling in primary T cells, Immunol Rev., vol. 229, No. 1, May 2009, pp. 114-125.

Roguska, et al., A comparison of two murine monoclonal antibodies humanized by CDR-grafting and variable domain resurfacing, Protein Eng., vol. 9, No. 10, Oct. 1996, pp. 895-904.

Roguska, et al., Humanization of murine monoclonal antibodies through variable domain resurfacing, Proc Natl Acad Sci U S A., vol. 91, No. 3, Feb. 1, 1994, pp. 969-973.

Sammartino, et al., Anti-GBM disease following CTLA4 blockade in a patient with metastatic melanoma, NDT Plus, vol. 3, No. 2, Apr. 2010, pp. 135-137.

Sandhu, Jasbir Singh, A rapid procedure for the humanization of monoclonal antibodies, Gene., vol. 150, No. 2, Dec. 15, 1994, pp. 409-410.

Studnicka, et al., Human-engineered monoclonal antibodies retain full specific binding activity by preserving non-CDR complementarity-modulating residues, Protein Eng., vol. 7, No. 6, Jun. 1994, pp. 805-814.

Taieb, et al., Chemoimmunotherapy of tumors: cyclophosphamide synergizes with exosome based vaccines, J Immunol., vol. 176, No. 5, Mar. 1, 2006, pp. 2722-2729.

Tan, et al., "Superhumanized" antibodies: reduction of immunogenic potential by complementarity-determining region grafting with human germline sequences: application to an anti-CD28, J Immunol., vol. 169, No. 2, Jul. 15, 2002, pp. 1119-1125.

Wang, et al., In vitro characterization of the anti-PD-1 antibody nivolumab, BMS-936558, and in vivo toxicology in non-human primates, Cancer Immunol Res., vol. 2, No. 9, Sep. 2014, pp. 846-856.

Weiss, R, Hot prospect for new gene amplifier, Science, vol. 254, No. 5036, Nov. 29, 1991, pp. 1292-1293.

International Search Report for PCT/US2023/061449 mailed Jul. 20, 2023.

Lee, et al., "Structural basis of checkpoint blockade by monoclonal antibodies in cancer immunotherapy", Nat Commun., vol. 7, No. 13354, Oct. 31, 2016, 10 pages.

\* cited by examiner

ANTIBODIES TO PROGRAMMED CELL DEATH PROTEIN 1

CROSS-REFERENCE TO RELATED APPLICATIONS

This application is a continuation of U.S. application Ser. No. 17/210,117, filed Mar. 23, 2021, which is a continuation of U.S. patent application Ser. No. 16/645,289, filed on Mar. 6, 2020, now U.S. Pat. No. 11,021,540, issued Jun. 1, 2021, which is a 371 Application of International Patent Application No. PCT/US2018/049854, filed on Sep. 7, 2018, and claims benefit of and priority to U.S. Provisional Application No. 62/555,156 filed on Sep. 7, 2017, U.S. Provisional Application No. 62/624,843 filed on Feb. 1, 2018, and U.S. Provisional Application No. 62/657,323 filed on Apr. 13, 2018, all of which are incorporated by reference in their entirety entireties.

REFERENCE TO SEQUENCE LISTING

The Sequence Listing submitted as a text file named "AURI_2017-034L_CON_2.xml," created on Sep. 5, 2023, and having a size of 45,478 bytes is hereby incorporated by reference pursuant to 37 C.F.R. § 1.52(e)(5).

TECHNICAL FIELD OF THE INVENTION

The invention is generally related to immunomodulation and to antibodies that specifically bind to PD-1 and methods of their use.

BACKGROUND OF THE INVENTION

The programmed cell death receptor protein (PD-1)/programmed cell death receptor protein ligand 1 (PD-L1) pathway has shown promising clinical success as a cancer immunotherapy target. Current antibodies that target either PD-1 or PD-L1 can block this interaction and boost the immune response against cancer cells. Successful clinical trials with PD-1 monoclonal antibodies and other immune-checkpoint inhibitors have opened new avenues in cancer immunology. However, the failure of a large subset of cancer patients to respond to new immunotherapies has led to intensified research on combination therapies and predictive biomarkers (Iwai, Y., et al., Journal of Biomedical Science, 24:26 (2017)).

Thus, it is an object of the invention to provide compositions and methods for modulating PD-1 signal transduction.

It is another object of the invention to provide antibodies and antigen binding fragments thereof that specifically bind to PD-1 and modulate PD-1 signal transduction.

It is another object of the invention to provide compositions and methods for treating cancer.

It is another object of the invention to provide compositions and methods for treating infections.

SUMMARY OF THE INVENTION

Antibodies and antigen binding fragments thereof are provided that immunospecifically bind to PD-1, preferably human or mouse PD-1, and induce or promote an immune response that activates immune cell proliferation or activity. In one embodiment, the disclosed antibodies and antigen binding fragments thereof specifically bind to PD-1 expressed on immune cells. The binding of the disclosed antibodies and antigen binding fragments thereof to PD-1 on immune cells causes an activating signal to be transmitted into the immune cell, for example a signal that enhances or promotes cytokine production and/or activation of immune cell proliferation. Immune cells that express PD-1, include but are not limited to B and T cells as well as myeloid-derived cells (Riley, J., Immunol Rev. 229(1):114-125 (2009)). In one embodiment, the immune cell is a T cell, preferably a CD8+ T cell.

Another embodiment provides a method of stimulating, promoting, or enhancing an adaptive immune response in a subject in need thereof by administering to the subject an effective amount of the disclosed anti-PD-1 antibodies or an antigen binding fragment thereof to induce, enhance, or promote an adaptive immune response in the subject.

One embodiment provides an antibody or antigen binding fragment thereof having heavy chain complementarity-determining regions (CDRs) having amino acid sequences according to SEQ ID NOs:6, 7, and 8, and light chain CDRs having amino acid sequences according to SEQ ID NOs:12, 13, and 14, wherein the antibody or antigen binding fragment thereof immunospecifically binds PD-1.

One embodiment provides an antibody or antigen binding fragment thereof having a heavy chain with at least 50%, 60%, 70%, 80%, 85%, 90%, 95%, 99%, or 100% sequence identity to SEQ ID NO:4 or 5.

One embodiment provides an antibody or antigen binding fragment thereof having a light chain with at least 50%, 60%, 70%, 80%, 85%, 90%, 95%, 99%, or 100% sequence identity to SEQ ID NO:10 or 11.

One embodiment provides an antibody or antigen binding fragment thereof any having a heavy chain with at least 50%, 60%, 70%, 80%, 85%, 90%, 95%, 99%, or 100% sequence identity to SEQ ID NO:4 or 5 and a light chain with at least 50%, 60%, 70%, 80%, 85%, 90%, 95%, 99%, or 100% sequence identity to SEQ ID NO:10 or 11.

One embodiment provides a transgenic animal engineered to express any one of the disclosed antibodies or antigen binding fragments thereof. In one embodiment, the animal is a mouse.

One embodiment provides a nucleic acid encoding a heavy chain with at least 50%, 60%, 70%, 80%, 85%, 90%, 95%, 99%, or 100% sequence identity to SEQ ID NO:4 or 5.

One embodiment provides a nucleic acid encoding a light chain with at least 50%, 60%, 70%, 80%, 85%, 90%, 95%, 99%, or 100% sequence identity to SEQ ID NO:10 or 11.

One embodiment provides an antibody or antigen binding fragment thereof having heavy chain CDRs having amino acid sequences according to SEQ ID NOs:18, 19, and 20, and light chain CDRs having amino acid sequences according to SEQ ID NOs:24, 13, and 25.

One embodiment provides an antibody or antigen binding fragment thereof having a heavy chain with at least 50%, 60%, 70%, 80%, 85%, 90%, 95%, 99%, or 100% sequence identity to SEQ ID NO:16 or 17.

One embodiment provides an antibody or antigen binding fragment thereof having a light chain with at least 50%, 60%, 70%, 80%, 85%, 90%, 95%, 99%, or 100% sequence identity to SEQ ID NO:22 or 23.

One embodiment provides an antibody or antigen binding fragment thereof having a heavy chain with at least 50%, 60%, 70%, 80%, 85%, 90%, 95%, 99%, or 100% sequence identity to SEQ ID NO:16 or 17 and a light chain with at least 50%, 60%, 70%, 80%, 85%, 90%, 95%, 99%, or 100% sequence identity to SEQ ID NO:22 or 23.

One embodiment provides a nucleic acid encoding a heavy chain with at least 50%, 60%, 70%, 80%, 85%, 90%, 95%, 99%, or 100% sequence identity to SEQ ID NO:16 or 17.

One embodiment provides a nucleic acid encoding a light chain with at least 50%, 60%, 70%, 80%, 85%, 90%, 95%, 99%, or 100% sequence identity to SEQ ID NO:22 or 23.

One embodiment provides an antibody or antigen binding fragment thereof having heavy chain CDRs having amino acid sequences according to SEQ ID NOs:29, 30, and 31, and light chain CDRs having amino acid sequences according to SEQ ID NOs:35, 36, and 37.

One embodiment provides an antibody or antigen binding fragment thereof having a heavy chain with at least 50%, 60%, 70%, 80%, 85%, 90%, 95%, 99%, or 100% sequence identity to SEQ ID NO:27 or 28.

One embodiment provides an antibody or antigen binding fragment thereof having a light chain with at least 50%, 60%, 70%, 80%, 85%, 90%, 95%, 99%, or 100% sequence identity to SEQ ID NO:33 or 34.

One embodiment provides an antibody or antigen binding fragment thereof having a heavy chain with at least 50%, 60%, 70%, 80%, 85%, 90%, 95%, 99%, or 100% sequence identity to SEQ ID NO:27 or 28 and a light chain with at least 50%, 60%, 70%, 80%, 85%, 90%, 95%, 99%, or 100% sequence identity to SEQ ID NO:33 or 34.

One embodiment provides a nucleic acid encoding a heavy chain with at least 50%, 60%, 70%, 80%, 85%, 90%, 95%, 99%, or 100% sequence identity to SEQ ID NO:27 or 28.

One embodiment provides a nucleic acid encoding a light chain with at least 50%, 60%, 70%, 80%, 85%, 90%, 95%, 99%, or 100% sequence identity to SEQ ID NO:33 or 34.

One embodiment provides an antibody, or antigen binding fragment thereof containing three light chain CDRs with amino acid sequences that are selected from the group consisting of SEQ ID NOs: 12, 13, 14, 24, 25, 35, 36, or 37.

Another embodiment provides an antibody, or antigen binding fragment thereof containing three heavy chain CDRs with amino acid sequences that are selected from the group consisting of SEQ ID NOs: 6, 7, 8, 18, 19, 20, 29, 30, or 31.

Another embodiment provides an antibody, or antigen binding fragment thereof containing three light chain CDRs with amino acid sequences that are selected from the group consisting of SEQ ID NOs: 12, 13, 14, 24, 25, 35, 36, or 37, and three heavy chain CDRs with amino acid sequences that are selected from the group consisting of SEQ ID NOs: 6, 7, 8, 18, 19, 20, 29, 30, or 31.

One embodiment provides an antibody or epitope binding fragment thereof or a fusion protein that immunospecifically binds to SEQ ID NO:38. In one embodiment the antibody binds to SEQ ID NO:38 on PD-1. In one embodiment, the antibody binds to PD-1 expressed on the surface of an immune cell and induces or promotes a signal through PD-1 that activates or stimulates the immune cell. In one embodiment the immune cell that is activated or stimulated is a T cell, for example a CD8$^+$ T cell.

In some embodiments, the antibody or antigen binding fragment thereof is human, mouse, chimeric, humanized, monoclonal, bispecific, trispecific or multispecific.

One embodiment provides a pharmaceutical composition including one or more of the disclosed antibodies or antigen binding fragments thereof. In some embodiments the pharmaceutical compositions include a second therapeutic agent and/or a pharmaceutically acceptable excipient. An exemplary second therapeutic agent includes cyclophosphamide.

One embodiment provides a method of inducing, promoting, or enhancing an immune response in a subject in need thereof by administering to the subject an effective amount of one or more of the disclosed antibodies or antigen binding fragments thereof to induce, promote, or enhance an immune response in the subject.

One embodiment provides a method for treating cancer in a subject in need thereof by administering to the subject an effective amount of one or more of the disclosed antibodies or antigen binding fragments thereof to treat cancer in the subject.

One embodiment provides a method for reducing tumor burden in a subject in need thereof by administering to the subject an effective amount of one or more of the disclosed antibodies or antigen binding fragments thereof to reduce tumor burden in the subject.

One embodiment provides a method for treating an infection in a subject in need thereof, by administering to the subject an effective amount of one or more of the disclosed antibodies or antigen binding fragments thereof to treat the infection in the subject.

DETAILED DESCRIPTION OF THE INVENTION

I. Definitions

Figure 1:
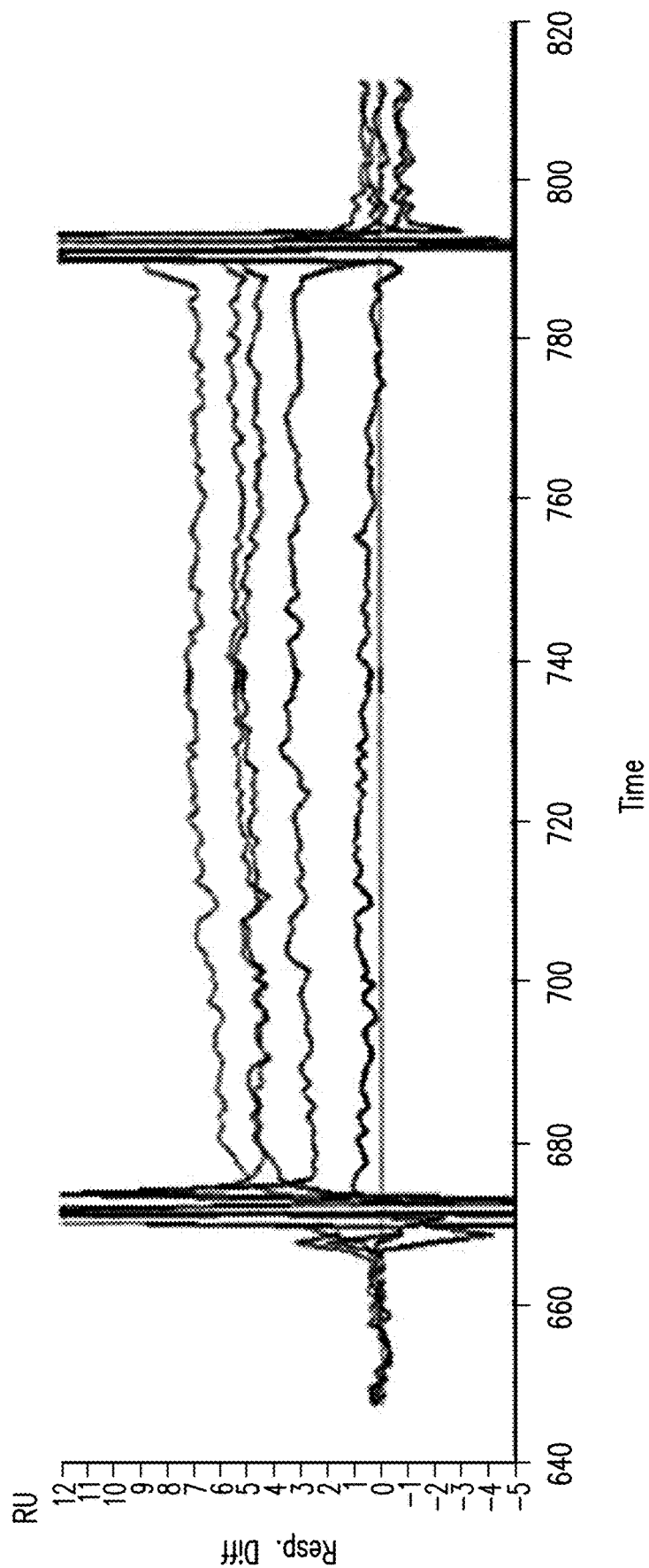
FIG. 1 is a graph showing the interaction kinetics as a function of time between monoclonal antibody 4G9 and human PD-1. The graph shows traces from concentrations of human PD-1 at 0, 125, 250, 500, 500, and 1000 nM.

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies,* vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The term "binding molecule," as used herein is intended to refer to molecules that specifically interact with and bind to a particular target. The target can comprise a biologic or small (chemical) molecule. The target molecule may define an antigen or antigenic moiety. Examples of a binding molecule include, but are not limited to, antibodies (including monoclonal antibodies, bispecific antibodies, as well as antibody fragments), fusion proteins, and other antigen-binding molecule known to those skilled in the art.

As used herein the term "modulate" relates to a capacity to alter an effect, result, or activity (e.g., signal transduction). Such modulation can agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. Preferably, such modulation will provide at least a 10% change in a measurable immune system activity, more preferably, at least a 50% change in such activity, or at least a 2-fold, 5-fold, 10-fold, or still more preferably, at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "co-stimulatory" signals encompass positive co-stimulatory signals (e.g., signals that result in enhancing an activity) and negative co-stimulatory signals (e.g., signals that result in inhibiting an activity).

As used herein, the term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. Preferably such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, preferably about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

As used herein, the term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder exacerbated by anti-PD-1 antibodies or an antigen fragment thereof.

As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "valency" refers to the number of binding sites available per molecule.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II WIC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, an "immunogenic agent" or "immunogen" is capable of inducing an immunological response against itself on administration to a mammal, optionally in conjunction with an adjuvant.

As used herein, the terms "individual," "host," "subject,: and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5);

tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "antigenic determinant" and "epitope" are used interchangeably and refer to the structure recognized by an antibody.

As used herein, a "conformational epitope" is an epitope that includes discontinuous sections of the antigen's amino acid sequence. Antibodies bind a conformational epitope based on 3-D surface features, shape, or tertiary structure of the antigen.

As used herein, a "linear epitope" is an epitope that formed by a continuous sequence of amino acids from the antigen. Linear epitopes typically include about 5 to about 10 continuous amino acid residues. Antibodies bind a linear epitope based on the primary sequence of the antigen.

As used herein, a "paratope," also called an "antigen-binding site," is a part of an antibody which recognizes and binds to an antigen.

II. Compositions

Antibodies and antigen binding fragments thereof that immunospecifically bind to PD-1 are provided. Contrary to the existing paradigm that PD-1 exclusively promotes a suppressive immune response (Riley, J., Immunol Rev. 229(1):114-125 (2009)), the disclosed antibodies and antigen binding fragments thereof, immunospecifically bind to PD-1 and cause an activating signal to be delivered to the immune cell that activates the immune cell rather than suppressing the immune cell.

A. Programmed Death Receptor Protein 1 (PD-1)

The disclosed antibodies and antigen binding fragments thereof immunospecifically bind to PD-1. The antibodies and antigen binding fragments thereof can bind to PD-1 having for example the amino acid sequences provide below.

Amino acid sequences for human PD-1 and mouse PD-1 are known in the art and include, for example, human PD-1

```
human PD-1
                                              (SEQ ID NO: 1)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL,
```

Accession: AJS10360 and which is specifically incorporated by reference in its entirety.

mouse PD-1

```
mouse PD-1
                                              (SEQ ID NO: 2)
MWVRQVPWSFTWAVLQLSWQSGWLLEVPNGPWRSLTFYPAWLTVSEGANA

TFTCSLSNWSEDLMLNWNRLSPSNQTEKQAAFCNGLSQPVQDARFQIIQL

PNRHDFHMNILDTRRNDSGIYLCGAISLHPKAKIEESPGAELVVTERILE

TSTRYPSPSPKPEGRFQGMVIGIMSALVGIPVLLLLAWALAVFCSTSMSE

ARGAGSKDDTLKEEPSAAPVPSVAYEELDFQGREKTPELPTACVHTEYAT

IVFTEGLGASAMGRRGSADGLQGPRPPRHEDGHCSWPL
```

UniProtKB-Q02242 (PDCD1_MOUSE) and which is specifically incorporated by reference in its entirety.

B. Antibody Compositions

The disclosed anti-PD-1 antibodies or antigen binding fragments thereof include whole immunoglobulin (i.e., an intact antibody) of any class, fragments thereof, and synthetic proteins containing at least the antigen binding variable domain of an antibody. In some embodiments, the disclosed antibody contains both an antibody light chain as well as at least the variable domain of an antibody heavy chain. In other embodiments, such molecules can further include one or more of the CH1, hinge, CH2, CH3, and CH4 regions of the heavy chain (especially, the CH1 and hinge regions, or the CH1, hinge and CH2 regions, or the CH1, hinge, CH2 and CH3 regions). The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain can be of the $IgG_2$ or $IgG_4$ class. The antibody can include sequences from more than one class or isotype, and selecting particular constant domains to optimize desired effector functions is within the ordinary skill in the art.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Some embodiments provide fragments of the anti-PD-1 antibodies which have bioactivity. The fragments, whether attached to other sequences or not, may include insertions, deletions, substitutions, or other selected modifications of particular regions or specific amino acids residues, provided the activity of the fragment is not significantly altered or impaired compared to the nonmodified antibody or antibody fragment.

Another embodiment provides single-chain antibodies specific to PD-1. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Another embodiment provides divalent single-chain variable fragments (di-scFvs) that can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Another embodiment provides a monoclonal antibody specific to PD-1 that induces an activating signal to immune cells. The monoclonal antibody can be obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

1. Chimeric and Humanized Antibodies

Another embodiment provides chimeric anti-PD-1 antibodies and antigen binding fragments thereof including one or more of the disclosed sequences and functional variants thereof are also provided that bind to PD-1 and cause an activating signal to be transmitted in to an immune cell expressing PD-1.

Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807, 715, 4,816,567, and 4,816,397. Chimeric antibodies including one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332).

The disclosed anti-PD-1 antibodies or antigen binding fragments thereof can be human or humanized antibodies, or antigen binding fragments thereof. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art, see, for example, European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J. Immunol.* 169:1119-1125; Caldas et al., 2000, *Protein Eng.* 13:353-360; Morea et al., 2000, *Methods* 20:267-79; Baca et al., 1997, *J. Biol. Chem.* 272:10678-10684; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-973; Jones et al., 1986, *Nature* 321:522-525; Reichmann et al., 1988, *Nature* 332:323-329; and Presta, 1992, *Curr. Op. Struct. Biol.* 2:593-596).

Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can be very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

A human, humanized or chimeric antibody derivative can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Such antibodies can also include at least a portion of an immunoglobulin constant region (Fc), typically that of a human immunoglobulin. The constant domains of such antibodies can be selected with respect to the proposed function of the antibody, in particular the effector function which may be required. In some embodiments, the constant domains of such antibodies are or can include human IgA, IgD, IgE, IgG or IgM domains. In a specific embodiment, human IgG constant domains, especially of the IgG1 and IgG3 isotypes are used, when the humanized antibody derivative is intended for a therapeutic use and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody is intended for therapeutic purposes and antibody effector function is not required.

Fc constant domains including one or more amino acid modifications which alter antibody effector functions such as those disclosed in U.S. Patent Application Publication Nos. 2005/0037000 and 2005/0064514.

The framework and CDR regions of a humanized antibody need not correspond precisely to the parental sequences, e.g., the donor CDR or the consensus framework can be mutagenized by substitution, insertion or deletion of at least one residue so that the CDR or framework residue at that site does not correspond to either the consensus or the donor antibody. In some embodiments, such mutations are not extensive. Usually, at least 75% of the humanized antibody residues will correspond to those of the parental framework region (FR) and CDR sequences, more often 90%, or greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos.

EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596.

Often, framework residues in the framework regions will be substituted with the corresponding residue from the CDR donor antibody to alter, for example improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, *Nature* 332:323).

Human, chimeric or humanized derivatives of the disclosed murine anti-human Siglec-15 antibodies can be used for in vivo methods in humans. Murine antibodies or antibodies of other species can be advantageously employed for many uses (for example, in vitro or in situ detection assays, acute in vivo use, etc.). Such a human or humanized antibody can include amino acid residue substitutions, deletions or additions in one or more non-human CDRs. The humanized antibody derivative can have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Such human antibodies can be made by a variety of methods known in the art including phage display methods using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Such human antibodies can be produced using transgenic mice which are incapable of expressing functional endogenous immunoglobulins, but which can express human immunoglobulin genes.

For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies can be engaged to provide human antibodies directed against a selected antigen using technology similar to that described above.

DNA sequences coding for human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions can be naturally occurring or consensus framework regions, and human framework regions (see, e.g., Chothia et al., 1998, "*Structural Determinants In The Sequences Of Immunoglobulin Variable Domain,*" *J. Mol. Biol.* 278: 457-479 for a listing of human framework regions).

C. Antibody Sequences 1. 4C12 Heavy Chain Sequences

One embodiment provides a murine monoclonal antibody or antigen binding fragment thereof isolated from hybridoma 4C12.

Another embodiment provides an antibody or antigen binding fragment thereof having a heavy chain encoded by a nucleic acid with at least 50%, 60%, 70%, 80%, 85%, 90%, 95%, 99%, or 100% sequence identity to:

(SEQ ID NO:3)
<u>ATGAGATGGAGCTGTATCATCCTCTTCTTGGTAGCAACAGCTACAGGTGTCCACTCC</u>CAGGTCCAAC

TGCAGCAGCCTGGGGCTGAACTGGTGAAGCCTGGGGCTTCAGTGAAGGTGTCCTGCAAGGCTTCTGG

CTACACCTTCACC<u>AGCTACTGGATGCAC</u>TGGGTGAAGCAGAGGCCTGGCCAAGGCCTTGAGTGGATT

GGAAGGATTCATCCTTCTGATAGTGATACTAACTACAATCAAAAGTTCAAGGGCAAGGCCACATTGA

-continued

```
CTGTAGACAAATCCTCCAGCACAGCCTACATGCAGCTCAGCAGCCTGACATCTGAGGACTCTGCGGT

CTATTACTGTGCACCCTATGGTAACTACGCCTCCGGGTTTGCTTACTGGGGCCAAGGGACTCTGGTC

ACTGTCTCTGCAGCCAAAACGACACCCCCATCTGTCTATCCACTGGCCCCTGGATCTGCTGCCCAAA

CTAACTCCATGGTGACCCTGGGATGCCTGGTCAAGGGCTATTTCCCTGAGCCAGTGACAGTGACCTG

GAACTCTGGATCCCTGTCCAGCGGTGTGCACACCTTCCCAGCTGTCCTGCAGTCTGACCTCTACACT

CTGAGCAGCTCAGTGACTGTCCCCTCCAGCACCTGGCCCAGCCAGACCGTCACCTGCAACGTTGCCC

ACCCGGCCAGCAGCACCAAGGTGGACAAGAAAATTGTGCCCAGGGATTGTGGTTGTAAGCCTTGCAT

ATGTACAGTCCCAGAAGTATCATCTGTCTTCATCTTCCCCCCAAAGCCCAAGGATGTGCTCACCATT

ACTCTGACTCCTAAGGTCACGTGTGTTGTGGTAGACATCAGCAAGGATGATCCCGAGGTCCAGTTCA

GCTGGTTTGTAGATGATGTGGAGGTGCACACAGCTCAGACGAAACCCCGGGAGGAGCAGATCAACAG

CACTTTCCGTTCAGTCAGTGAACTTCCCATCATGCACCAGGACTGGCTCAATGGCAAGGAGTTCAAA

TGCAGGGTCAACAGTGCAGCTTTCCCTGCCCCCATCGAGAAAACCATCTCCAAAACCAAAGGCAGAC

CGAAGGCTCCACAGGTGTACACCATTCCACCTCCCAAGGAGCAGATGGCCAAGGATAAAGTCAGTCT

GACCTGCATGATAACAAACTTCTTCCCTGAAGACATTACTGTGGAGTGGCAGTGGAATGGGCAGCCA

GCGGAGAACTACAAGAACACTCAGCCCATCATGGACACAGATGGCTCTTACTTCGTCTACAGCAAGC

TCAATGTGCAGAAGAGCAACTGGGAGGCAGGAAATACTTTCACCTGCTCTGTGTTACATGAGGGCCT

GCACAACCACCATACTGAGAAGAGCCTCTCCCACTCTCCTGGTAAATGA.
```

Underlined sequences correspond to complementarity determining regions (CDRs). Double underline sequence corresponds to the constant region. Dashed underlined sequences correspond to the leader sequence.

The nucleic acid can be in a vector, for example an expression vector. The nucleic acid can be extrachromosal on inserted into a chromosome of a host cell, for example a Chinese Hamster Ovary cell.

One embodiment provides an antibody or antigen binding fragment thereof having heavy chain with an amino acid sequence having at least 50%, 60%, 70%, 80%, 85%, 90%, 95%, 99%, or 100% sequence identity to:

(SEQ ID NO:4)

MRWSCIILFLVATATGVHSQVQLQQPGAELVKPGASVKVSCKASGYTFTSYWMHWVKQRPGQGLEWI

GRIHPSDSDTNYNQKFKGKATLTVDKSSSTAYMQLSSLTSEDSAVYYCAPYGNYASGFAYWGQGTLV

TVSAAKTTPPSVYPLAPGSAAQTNSMVTLGCLVKGYFPEPVTVTWNSGSLSSGVHTFPAVLQSDLYT

LSSSVTVPSSTWPSQTVTCNVAHPASSTKVDKKIVPRDCGCKPCICTVPEVSSVFIFPPKPKDVLTI

TLTPKVTCVVVDISKDDPEVQFSWFVDDVEVHTAQTKPREEQINSTFRSVSELPIMHQDWLNGKEFK

CRVNSAAFPAPIEKTISKTKGRPKAPQVYTIPPPKEQMAKDKVSLTCMITNFFPEDITVEWQWNGQP

AENYKNTQPIMDTDGSYFVYSKLNVQKSNWEAGNTFTCSVLHEGLHNHHTEKSLSHSPGK

Single underline corresponds to the leader sequence. Double under line corresponds to CDRs, and dashed underline corresponds to the constant region.

Another embodiment provides an antibody or antigen binding fragment thereof having heavy chain without the leader sequence with an amino acid sequence having at least 50%, 60%, 70%, 80%, 85%, 90%, 95%, 99%, or 100% sequence identity to:

(SEQ ID NO: 5)

QVQLQQPGAELVKPGASVKVSCKASGYTFTSYWMHWVKQRPGQGLEWIGRIHPSDSDTNYNQKFKGKAT

LTVDKSSSTAYMQLSSLTSEDSAVYYCAPYGNYASGFAYWGQGTLVTVSAAKTTPPSVYPLAPGSAAQTN

SMVTLGCLVKGYFPEPVTVTWNSGSLSSGVHTFPAVLQSDLYTLSSSVTVPSSTWPSQTVTCNVAHPASST

```
KVDKKIVPRDCGCKPCICTVPEVSSVFIFPPKPKDVLTITLTPKVTCVVVDISKDDPEVQFSWFVDDVEVHTA

QTKPREEQINSTFRSVSELPIMHQDWLNGKEFKCRVNSAAFPAPIEKTISKTKGRPKAPQVYTIPPPKEQMAK

DKVSLTCMITNFFPEDITVEWQWNGQPAENYKNTQPIMDTDGSYFVYSKLNQQKSNWEAGNTFTCSVLHE

GLHNHHTEKSLSHSPGK.
```

Double under line corresponds to CDRs, and broken underline corresponds to the constant region.

The amino acid sequence for CDR1 of the 4C12 heavy chain is SYWMH (SEQ ID NO:6).

The amino acid sequence for CDR2 of the 4C12 heavy chain is RIHPSDSDTNYNQKFKG (SEQ ID NO:7).

The amino acid sequence for CDR3 of the 4C12 heavy chain is YGNYASGFAY (SEQ ID NO:8).

One embodiment provides an antibody or antigen binding fragment thereof having a heavy chain according to SEQ ID NO:4 or 5.

Another embodiment provides and antibody or antigen binding fragment thereof having a heavy chain encoded by a nucleic acid with at least 50%, 60%, 70%, 80%, 85%, 90%, 95%, 99%, or 100% sequence identity to SEQ ID NO:3.

One embodiment provides an antibody having three different CDRs selected from the group consisting of SEQ ID NO: 6, 7, and 8.

2. 4C12 Light Chain Sequences

Another embodiment provides an antibody or antigen binding fragment thereof having a light chain encoded by a nucleic acid with at least 50%, 60%, 70%, 80%, 85%, 90%, 95%, 99%, or 100% sequence identity to:

```
                                                                (SEQ ID NO: 9)
ATGGGCATCAAGATGGAGTCACAGATTCAGGCATTTGTATTCGTGTTTCTCTGGTTGTCTGGTGTTG

ACGGAGACATTGTGATGACCCAGTCTCACAAATTCATGTCCACATCAGTAGGAGACAGGGTCAGCAT

CACCTGCAAGGCCAGTCAGGATGTGAGTACTGCTGTAGCCTGGTATCAACAAAAACCAGGGCAATCT

CCTAAACTACTGATTTACTGGGCATCCACCCGGCACACTGGAGTCCCTGATCGCTTCACAGGCAGTG

GATCTGGGACAGATTATACTCTCACCATCAGCAGTGTGCAGGCTGAAGACCTGGCACTTTATTACTG

TCAGCAACATTATAGCACTCCGTGGACGTTCGGTGGAGGCACCAAGCTGGAAATCAAACGGGCTGAT

GCTGCACCAACTGTATCCATCTTCCCACCATCCAGTGAGCAGTTAACATCTGGAGGTGCCTCAGTCG

TGTGCTTCTTGAACAACTTCTACCCCAAAGACATCAATGTCAAGTGGAAGATTGATGGCAGTGAACG

ACAAAATGGCGTCCTGAACAGTTGGACTGATCAGGACAGCAAAGACAGCACCTACAGCATGAGCAGC

ACCCTCACGTTGACCAAGGACGAGTATGAACGACATAACAGCTATACCTGTGAGGCCACTCACAAGA

CATCAACTTCACCCATTGTCAAGAGCTTCAACAGGAATGAGTTAG
```

Dashed underline represents the leader sequence. Single underline represents the CDRs. Double underline represents the constant region.

The nucleic acid can be in a vector, for example an expression vector. The nucleic acid can be extrachromosal on inserted into a chromosome of a host cell, for example a Chinese Hamster Ovary cell.

Another embodiment provides an antibody or antigen binding fragment thereof having a light chain having an amino acid sequence with at least 50%, 60%, 70%, 80%, 85%, 90%, 95%, 99%, or 100% sequence identity to:

```
                                                               (SEQ ID NO: 10)
MGIKMESQIQAFVFVFLWLSGVDGDIVMTQSHKFMSTSVGDRVSITCKASQDVSTAVAWYQQKPQS

PKLLIYWASTRHTGVPDRFTGSGSGTDYTLTISSVQAEDLALYYCQQHYSTPWTFGGGTKLEIKRAD

AAPTVSIFPPSSEQLTSGGASVVCFLNNFYPKDINVKWKIDGSERQNGVLNSWTDQDSKDSTYSMSS

TLTLTKDEYERHNSYTCEATHKTSTSPIVKSFNRNEC.
```

Another embodiment provides an antibody or antigen binding fragment thereof having a light chain without the leader sequence having an amino acid sequence with at least 50%, 60%, 70%, 80%, 85%, 90%, 95%, 99%, or 100% sequence identity to:

(SEQ ID NO: 11)
DIVMTQSHKFMSTSVGDRVSITC<u>KASQDVSTAVA</u>WYQQKPGQSPKLLIY<u>WASTRHT</u>GVPDRFTGSGSGTD
YTLTISSVQAEDLALYYC<u>QQHYSTPWT</u>FGGGTKLEIKRADAAPTVSIFPPSSEQLTSGGASVVCFLNNFYPK
DINVKWKIDGSERQNGVLNSWTDQDSKDSTYSMSSTLTLTKDEYERHNSYTCEATHKTSTSPIVKSFNRNE
C.

Double underline represents CDRs. Dashed underline represents the constant region.

The amino acid sequence for CDR1 of the 4C12 light chain is KASQDVSTAVA (SEQ ID NO:12).

The amino acid sequence for CDR2 of the 4C12 light chain is WASTRHT (SEQ ID NO:13).

The amino acid sequence for CDR3 of the 4C12 light chain is QQHYSTPWT (SEQ ID NO:14).

One embodiment provides an antibody or antigen binding fragment thereof having a light chain with at least 50%, 60%, 70%, 80%, 85%, 90%, 95%, 99%, or 100% sequence identity to SEQ ID NO:10 or 11.

Another embodiment provides and antibody or antigen binding fragment thereof having a light chain encoded by a nucleic acid with at least 50%, 60%, 70%, 80%, 85%, 90%, 95%, 99%, or 100% sequence identity to SEQ ID NO:9.

One embodiment provides an antibody having three different CDRs selected from the group consisting of SEQ ID NO: 12, 13, and 14.

Another embodiment provides an antibody or antigen binding fragment thereof having a heavy chain with an amino acid sequence having at least 50%, 60%, 70%, 80%, 85%, 90%, 95%, 99%, or 100% sequence identity to SEQ ID NO:4 or 5 and light chain with an amino acid sequence at least 50%, 60%, 70%, 80%, 85%, 90%, 95%, 99%, or 100% sequence identity to SEQ ID NO:10 or 11, or light and heavy chain combinations thereof.

Another embodiment provides an antibody or antigen binding fragment thereof having three different heavy chain CDRs with an amino acid selected from the group consisting of SEQ ID NOs:6, 7, and 8 and three different light chain CDRs with amino acids selected from the group consisting of SEQ ID NOs: 12, 13, and 14.

3. 2B5 Heavy Chain Sequences

One embodiment provides a murine monoclonal antibody or antigen binding fragment thereof isolated from hybridoma 2B5.

Another embodiment provides an antibody or antigen binding fragment thereof having a heavy chain encoded by a nucleic acid with at least 50%, 60%, 70%, 80%, 85%, 90%, 95%, 99%, or 100% sequence identity to:

(SEQ ID NO: 15)
<u>ATGGAATGGAGCAGAGTCTTTATCTTTCTCCTATCAGTAACTGCAGGTGTTCACTCCCAGGTCCAGC</u>
TGCAGCAGTCTGGAGCTGAGCTGGTAAGGCCTGGGACTTCAGTGAAGGTGTCCTGCAAGGCTTCTGG
ATACGCCTTCACT<u>AATTACTTGATAGAGTGGGTAAAGCAGAGGCCTGGACAGGGCCTTGAGTGGATT
GGA</u>GTGATTAATCCTGGAAGTGGTGGTACTAACTACAATGAGAAGTTCAAGGGCAAGGCAACACTGA
CTGCAGACAAATCCTCCAGCACTGCCTACATGCAGCTCAGCAGCCTGACATCTGAGGACTCTGCGGT
CTATTTCTGTGCAAGATCAGCT<u>CAGGCCCCTGACTACTGGGGCCAAGGCACCACTCTCACAGTCTCC</u>
<u>TCAGAGAGTCAGTCCTTCCCAAATGTCTTCCCCCTCGTCTCCTGCGAGAGCCCCCTGTCTGATAAGA</u>
<u>ATCTGGTGGCCATGGGCTGCCTGGCCCGGGACTTCCTGCCCAGCACCATTTCCTTCACCTGGAACTA</u>
<u>CCAGAACAACACTGAAGTCATCCAGGGTATCAGAACCTTCCCAACACTGAGGACAGGGGGCAAGTAC</u>
<u>CTAGCCACCTCGCAGGTGTTGCTGTCTCCCAAGAGCATCCTTGAAGGTTCAGATGAATACCTGGTAT</u>
<u>GCAAAATCCACTACGGAGGCAAAAACAAAGATCTGCATGTGCCCATTCCAGCTGTCGCAGAGATGAA</u>
<u>CCCCAATGTAAATGTGTTCGTCCCACCACGGGATGGCTTCTCTGGCCCTGCACCACGCAAGTCTAAA</u>
<u>CTCATCTGCGAGGCCACGAACTTCACTCCAAAACCGATCACAGTATCCTGGCTAAAGGATGGGAAGC</u>
<u>TCGTGGAATCTGGCTTCACCACAGATCCGGTGACCATCGAGAACAAAGGATCCACACCCCAAACCTA</u>
<u>CAAGGTCATAAGCACACTTACCATCTCTGAAATCGACTGGCTGAACCTGAATGTGTACACCTGCCGT</u>

-continued

```
GTGGATCACAGGGGTCTCACCTTCTTGAAGAACGTGTCCTCCACATGTGCTGCCAGTCCCTCCACAG

ACATCCTAACCTTCACCATCCCCCCTCCTTTGCCGACATCTTCCTCAGCAAGTCCGCTAACCTGAC

CTGTCTGGTCTCAAACCTGGCAACCTATGAAACCCTGAATATCTCCTGGGCTTCTCAAAGTGGTGAA

CCACTGGAAACCAAAATTAAAATCATGGAAAGCCATCCCAATGGCACCTTCAGTGCTAAGGGTGTGG

CTAGTGTTTGTGTGGAAGACTGGAATAACAGGAAGGAATTTGTGTGTACTGTGACTCACAGGGATCT

GCCTTCACCACAGAAGAAATTCATCTCAAAACCCAATGAGGTGCACAAACATCCACCTGCTGTGTAC

CTGCTGCCACCAGCTCGTGAGCAACTGAACCTGAGGGAGTCAGCCACAGTCACCTGCCTGGTGAAGG

GCTTCTCTCCTGCAGACATCAGTGTGCAGTGGCTTCAGAGAGGGCAACTCTTGCCCCAAGAGAAGTA

TGTGACCAGTGCCCCGATGCCAGAGCCTGGGGCCCCAGGCTTCTACTTTACCCACAGCATCCTGACT

GTGACAGAGGAGGAATGGAACTCCGGAGAGACCTATACCTGTGTTGTAGGCCACGAGGCCCTGCCAC

ACCTGGTGACCGAGAGGACCGTGGACAAGTCCACTGGTAAACCCACACTGTACAATGTCTCCCTGAT

CATGTCTGACACAGGCGGCACCTGCTATTGA .
```

Underlined sequences correspond to complementarity determining regions (CDRs). Double underline sequence corresponds to the constant region. Dashed underlined sequences correspond to the leader sequence.

The nucleic acid can be in a vector, for example an expression vector. The nucleic acid can be extrachromosal on inserted into a chromosome of a host cell, for example a Chinese Hamster Ovary cell.

One embodiment provides an antibody or antigen binding fragment thereof having heavy chain with an amino acid sequence having at least 50%, 60%, 70%, 80%, 85%, 90%, 95%, 99%, or 100% sequence identity to:

(SEQ ID NO: 16)
```
MEWSRVFIFLLSVTAGVHSQVQLQQSGAELVRPGTSVKVSCKASGYAFTNYLIEWVKQRPGQGLEWI

GVINPGSGGTNYNEKFKGKATLTADKSSSTAYMQLSSLTSEDSAVYFCARSAQAPDYWGQGTTLTVS

SESQSFPNVFPLVSCESPLSDKNLVAMGCLARDFLPSTISFTWNYQNNTEVIQGIRTFPTLRTGGKY

LATSQVLLSPKSILEGSDEYLVCKIHYGGKNKDLHVPIPAVAEMNPNVNVFVPPRDGFSGPAPRKSK

LICEATNFTPKPITVSWLKDGKLVESGFTTDPVTIENKGSTPQTYKVISTLTISEIDWLNLNVYTCR

VDHRGLTFLKNVSSTCAASPSTDILTFTIPPSFADIFLSKSANLTCLVSNLATYETLNISWASQSGE

PLETKIKIMESHPNGTFSAKGVASVCVEDWNNRKEFVCTVTHRDLPSPQKKFISKPNEVHKHPPAVY

LLPPAREQLNLRESATVTCLVKGFSPADISVQWLQRGQLLPQEKYVTSAPMPEPGAPGFYFTHSILT

VTEEEWNSGETYTCVVGHEALPHLVTERTVDKSTGKPTLYNVSLIMSDTGGTCY .
```

Single underline corresponds to the leader sequence. Double under line corresponds to CDRs, and dashed underline corresponds to the constant region.

Another embodiment provides an antibody or antigen binding fragment thereof having heavy chain without the leader sequence with an amino acid sequence having at least 50%, 60%, 70%, 80%, 85%, 90%, 95%, 99%, or 100% sequence identity to:

(SEQ ID NO: 17)
```
QVQLQQSGAELVRPGTSVKVSCKASGYAFTNYLIEWVKQRPGQGLEWIGVINPGSGGTNYNEKFKGKATL

TADKSSSTAYMQLSSLTSEDSAVYFCARSAQAPDYWGQGTTLTVSSESQSFPNVFPLVSCESPLSDKNLVA

MGCLARDFLPSTISFTWNYQNNTEVIQGIRTFPTLRTGGKYLATSQVLLSPKSILEGSDEYLVCKIHYGGKN

KDLHVPIPAVAEMNPNVNVFVPPRDGFSGPAPRKSKLICEATNFTPKPITVSWLKDGKLVESGFTTDPVTIE

NKGSTPQTYKVISTLTISEIDWLNLNVYTCRVDHRGLTFLKNVSSTCAASPSTDILTFTIPPSFADIFLSKSANL

TCLVSNLATYETLNISWASQSGEPLETKIKIMESHPNGTFSAKGVASVCVEDWNNRKEFVCTVTHRDLPSP
```

-continued

QKKFISKPNEVHKHPPAVYLLPPAREQLNLRESATVTCLVKGFSPADISVQWLQRGQLLPQEKYVTSAPMP

EPGAPGFYFTHSILTVTEEEWNSGETYTCVVGHEALPHLVTERTVDKSTGKPTLYNVSLIMSDTGGTCY.

Double under line corresponds to CDRs, and dashed underline corresponds to the constant region.

The amino acid sequence for CDR1 of the 2B5 heavy chain is NYLIE (SEQ ID NO:18).

The amino acid sequence for CDR2 of the 2B5 heavy chain is VINPGSGGTNYNEKFKG (SEQ ID NO:19).

The amino acid sequence for CDR3 of the 2B5 heavy chain is SAQAPDY (SEQ ID NO:20).

One embodiment provides an antibody or antigen binding fragment thereof having a heavy chain according to SEQ ID NO:16 or 17.

Another embodiment provides and antibody or antigen binding fragment thereof having a heavy chain encoded by a nucleic acid with at least 50%, 60%, 70%, 80%, 85%, 90%, 95%, 99%, or 100% sequence identity to SEQ ID NO:15.

One embodiment provides an antibody having three different CDRs selected from the group consisting of SEQ ID NO: 18, 19, and 20.

4. 2B5 Light Chain Sequences

Another embodiment provides an antibody or antigen binding fragment thereof having a light chain encoded by a nucleic acid with at least 50%, 60%, 70%, 80%, 85%, 90%, 95%, 99%, or 100% sequence identity to:

(SEQ ID NO: 21)

ATGGGCATCAAGATGGAGACACATTCTCAGGTCTTTGTATACATGTTGCTGTGGTTGTCTGGTGTTG

AAGGAGACATTGTGATGACCCAGTCTCACAAATTCATGTCCACATCAGTAGGAGACAGGGTCAGCAT

CACCTGCAAGGCCAGTCAGGATGTGGGTACTGCTGTAGCCTGGTATCAACAGAAACCAGGGCAATCT

CCTAAACTACTGATTTACTGGGCATCCACCCGGCACACTGGAGTCCCTGATCGCTTCACAGGCAGTG

GATCTGGGACAGATTTCACTCTCACCATTAGCAATGTGCAGTCTGAAGACTTGGCAGATTATTTCTG

TCAGCAATATAGCAGCTATCCATTCACGTTCGGCTCGGGGACAAAGTTGGAAATAAAACGGGCTGAT

GCTGCACCAACTGTATCCATCTTCCCACCATCCAGTGAGCAGTTAACATCTGGAGGTGCCTCAGTCG

TGTGCTTCTTGAACAACTTCTACCCCAAAGACATCAATGTCAAGTGGAAGATTGATGGCAGTGAACG

ACAAAATGGCGTCCTGAACAGTTGGACTGATCAGGACAGCAAAGACAGCACCTACAGCATGAGCAGC

ACCCTCACGTTGACCAAGGACGAGTATGAACGACATAACAGCTATACCTGTGAGGCCACTCACAAGA

CATCAACTTCACCCATTGTCAAGAGCTTCAACAGGAATGAGTGTTAG.

Dashed underline represents the leader sequence. Single underline represents the CDRs. Double underline represents the constant region.

The nucleic acid can be in a vector, for example an expression vector. The nucleic acid can be extrachromosal on inserted into a chromosome of a host cell, for example a Chinese Hamster Ovary cell.

Another embodiment provides an antibody or antigen binding fragment thereof having a light chain having an amino acid sequence with at least 50%, 60%, 70%, 80%, 85%, 90%, 95%, 99%, or 100% sequence identity to:

(SEQ ID NO: 22)

MGIKMETHSQVFVYMLLWLSGVEGDIVMTQSHKFMSTSVGDRVSITCKASQDVGTAVAWYQQKPGQS

PKLLIYWASTRHTGVPDRFTGSGSGTDFTLTISNVQSEDLADYFCQQYSSYPFTFGSGTKLEIKRAD

AAPTVSIFPPSSEQLTSGGASVVCFLNNFYPKDINVKWKIDGSERQNGVLNSWTDQDSKDSTYSMSS

TLTLTKDEYERHNSYTCEATHKTSTSPIVKSFNRNEC.

Underline represents the leader sequence. Double underline represents CDRs. Dashed underline represents the constant region.

Another embodiment provides an antibody or antigen binding fragment thereof having a light chain without the leader sequence having an amino acid sequence with at least 50%, 60%, 70%, 80%, 85%, 90%, 95%, 99%, or 100% sequence identity to:

(SEQ ID NO: 23)
DIVMTQSHKFMSTSVGDRVSITC<u>KASQDVSTAVA</u>WYQQKPGQSPKLLIY<u>WASTRHT</u>GVPDRFTGSGSGTD

YTLTISSVQAEDLALYYC<u>QQHYSTPWT</u>FFGGGTKLEIKRADAAPTVSIFPPSSEQLTSGGASVVCFLNNFYPK

DINVKWKIDGSERQNGVLNSWTDQDSKDSTYSMSSTLTLTKDEYERHNSYTCEATHKTSTSPIVKSFNRNE

C.

Double underline represents CDRs. Dashed underline represents the constant region.

The amino acid sequence for CDR1 of the 2B5 light chain is KASQDVSTAVA (SEQ ID NO:24).

The amino acid sequence for CDR2 of the 2B5 light chain is WASTRHT (SEQ ID NO:13).

The amino acid sequence for CDR3 of the 2B5 light chain is QQHYSTPWT (SEQ ID NO:25).

One embodiment provides an antibody or antigen binding fragment thereof having a light chain with at least 50%, 60%, 70%, 80%, 85%, 90%, 95%, 99%, or 100% sequence identity to SEQ ID NO:22 or 23.

Another embodiment provides and antibody or antigen binding fragment thereof having a light chain encoded by a nucleic acid with at least 50%, 60%, 70%, 80%, 85%, 90%, 95%, 99%, or 100% sequence identity to SEQ ID NO:21.

One embodiment provides an antibody having three different CDRs selected from the group consisting of SEQ ID NO: 24, 13, and 25.

Another embodiment provides an antibody or antigen binding fragment thereof having a heavy chain with an amino acid sequence having at least 50%, 60%, 70%, 80%, 85%, 90%, 95%, 99%, or 100% sequence identity to SEQ ID NO:16 or 17 and light chain with an amino acid sequence at least 50%, 60%, 70%, 80%, 85%, 90%, 95%, 99%, or 100% sequence identity to SEQ ID NO:22 or 23, or light and heavy chain combinations thereof.

Another embodiment provides an antibody or antigen binding fragment thereof having three different heavy chain CDRs with an amino acid selected from the group consisting of SEQ ID NOs:18, 19, and 20 and three different light chain CDRs with amino acids selected from the group consisting of SEQ ID NOs: 24, 13, and 25.

6. 4G9 Heavy Chain Sequences

One embodiment provides a murine monoclonal antibody or antigen binding fragment thereof isolated from hybridoma 4G9.

Another embodiment provides an antibody or antigen binding fragment thereof having a heavy chain encoded by a nucleic acid with at least 50%, 60%, 70%, 80%, 85%, 90%, 95%, 99%, or 100% sequence identity to:

(SEQ ID NO: 26)
<u>ATGGGTTGGCTGTGGAACTTGCTATTCCTGATGGCAGCTGCCCAAAGTGCCCAAGC</u>ACAGATCCAGT

TGGTACAGTCTGGACCTGAGCTGAAGAAGCCTGGAGAGACAGTCAAGATCTCCTGCAAGGCTTCTGG

GTATACCTTCACA<u>ACCTATGGAATGACC</u>TGGGTGAAACAGGCTCCAGGAAAGGGTTTAAAGTGGATG

GGCTGGATAAACACCTACTCTGGAGTGCCAACATATGCTGATGACTTCAAGGGACGGTTTGCCTTCT

CTTTGGAAACCTCTGCCAGCACTGCCTATTTGCAGATCAACAACCTCAAAAATGAGGACACGGCTAC

ATATTTCTGTGCAAGA<u>GGGGGACGGGGGTTTGCTTACTGGGGCCAAGGG</u>ACTCTGGTCACTGTCTCT

<span style="border-bottom: 1px dashed">GCAGCCAAAACAACACCCCCATCAGTCTATCCACTGGCCCCTGGGTGTGGAGATACAACTGGTTCCT</span>

<span style="border-bottom: 1px dashed">CTGTGACTCTGGGATGCCTGGTCAAGGGCTACTTCCCTGAGTCAGTGACTGTGACTTGGAACTCTGG</span>

<span style="border-bottom: 1px dashed">ATCCCTGTCCAGCAGTGTGCACACCTTCCCAGCTCTCCTGCAGTCTGGACTCTACACTATGAGCAGC</span>

<span style="border-bottom: 1px dashed">TCAGTGACTGTCCCCTCCAGCACCTGGCCAAGTCAGACCGTCACCTGCAGCGTTGCTCACCCAGCCA</span>

<span style="border-bottom: 1px dashed">GCAGCACCACGGTGGACAAAAAACTTGAGCCCAGCGGGCCCATTTCAACAATCAACCCCTGTCCTCC</span>

<span style="border-bottom: 1px dashed">ATGCAAGGAGTGTCACAAATGCCCAGCTCCTAACCTCGAGGGTGGACCATCCGTCTTCATCTTCCCT</span>

<span style="border-bottom: 1px dashed">CCAAATATCAAGGATGTACTCATGATCTCCCTGACACCCAAGGTCACGTGTGTGGTGGTGGATGTGA</span>

<span style="border-bottom: 1px dashed">GCGAGGATGACCCAGACGTCCGGATCAGCTGGTTTGTGAACAACGTGGAAGTACACACAGCTCAGAC</span>

<span style="border-bottom: 1px dashed">ACAAACCCATAGAGAGGATTACAACAGTACTATCCGGGTGGTCAGTGCCCTCCCCATCCAGCACCAG</span>

-continued

GACTGGATGAGTGGCAAGGAGTTCAAATGCAAGGTCAACAACAAAGACCTCCCATCACCCATCGAGA

GAACCATCTCAAAAATTAAAGGGCTAGTCAGAGCTCCACAAGTATACATCTTGCCGCCACCAGCAGA

GCAGTTGTCCAGGAAAGATGTCAGTCTCACTTGCCTGGTCGTGGGCTTCAACCCTGGAGACATCAGT

GTGGAGTGGACCAGCAATGGGCATACAGAGGAGAACTACAAGGACACCGCACCAGTCCTGGACTCTG

ACGGTTCTTACTTCATATACAGCAAGCTCGATATAAAAACAAGCAAGTGGGAGAAAACAGATTCCTT

CTCATGCAACGTGAGACACGAGGGTCTGAAAAATTACTACCTGAAGAAGACCATCTCCCGGTCTCCG

GGTAAATGA.

Underlined sequences correspond to complementarity determining regions (CDRs). Double underline sequence corresponds to the constant region. Dashed underlined sequences correspond to the leader sequence.

The nucleic acid can be in a vector, for example an expression vector. The nucleic acid can be extrachromosal on inserted into a chromosome of a host cell, for example a Chinese Hamster Ovary cell.

One embodiment provides an antibody or antigen binding fragment thereof having heavy chain with an amino acid sequence having at least 50%, 60%, 70%, 80%, 85%, 90%, 95%, 99%, or 100% sequence identity to:

Double under line corresponds to CDRs, and dashed underline corresponds to the constant region.

The amino acid sequence for CDR1 of the 4G9 heavy chain is TYGMT (SEQ ID NO:29).

The amino acid sequence for CDR2 of the 4G9 heavy chain is WINTYSGVPTYADDFKG (SEQ ID NO:30).

The amino acid sequence for CDR3 of the 4G9 heavy chain is GGRGFAY (SEQ ID NO:31).

One embodiment provides a 4G9 antibody or antigen binding fragment thereof having a heavy chain according to SEQ ID NO:27 or 28.

(SEQ ID NO: 27)
MGWLWNLLFLMAAAQSAQAQIQLVQSGPELKKPGETVKISCKASGYTFTTYGMTWVKQAPGKGLKWM

GWINTYSGVPTYADDFKGRFAFSLETSASTAYLQINNLKNEDTATYFCARGGRGFAYWGQGTLVTVS

AAKTTPPSVYPLAPGCGDTTGSSVTLGCLVKGYFPESVTVTWNSGSLSSSVHTFPALLQSGLYTMSS

SVTVPSSTWPSQTVTCSVAHPASSTTVDKKLEPSGPISTINPCPPCKECHKCPAPNLEGGPSVFIFP

PNIKDVLMISLTPKVTCVVVDVSEDDPDVRISWFVNNVEVHTAQTQTHREDYNSTIRVVSALPIQHQ

DWMSGKEFKCKVNNKDLPSPIERTISKIKGLVRAPQVYILPPPAEQLSRKDVSLTCLVVGFNPGDIS

VEWTSNGHTEENYKDTAPVLDSDGSYFIYSKLDIKTSKWEKTDSFSCNVRHEGLKNYYLKKTISRSP

GK.

Single underline corresponds to the leader sequence. Double under line corresponds to CDRs, and dashed underline corresponds to the constant region.

Another embodiment provides an antibody or antigen binding fragment thereof having heavy chain without the leader sequence with an amino acid sequence having at least 50%, 60%, 70%, 80%, 85%, 90%, 95%, 99%, or 100% sequence identity to:

Another embodiment provides a 4G9 antibody or antigen binding fragment thereof having a heavy chain encoded by a nucleic acid with at least 50%, 60%, 70%, 80%, 85%, 90%, 95%, 99%, or 100% sequence identity to SEQ ID NO:26.

One embodiment provides a 4G9 antibody having three different CDRs selected from the group consisting of SEQ ID NO: 29, 30, and 31.

(SEQ ID NO: 28)
QIQLVQSGPELKKPGETVKISCKASGYTFTTYGMTWVKQAPGKGLKWMGWINTYSGVPTYADDFKGRFA

FSLETSASTAYLQINNLKNEDTATYFCARGGRGFAYWGQGTLVTVSAAKTTPPSVYPLAPGCGDTTGSSVT

LGCLVKGYFPESVTVTWNSGSLSSSVHTFPALLQSGLYTMSSSVTVPSSTWPSQTVTCSVAHPASSTTVDKK

LEPSGPISTINPCPPCKECHKCPAPNLEGGPSVFIDPPNIKDVLMISLTPKVTCVVVDVSEDDPDVRISWFVNN

VEVHTAQTQTHREDYNSTIRVVSALPIQHQDWMSGKEFKCKVNNKDLPSPIERTISKIKGLVRAPQVYILPP

PAEQLSRKDVSLTCLVVGFNPGDISVEWTSNGHTEENYKDTAPVLDSDGSYFIYSKLDIKTSKWEKTDSFSC

NVRHEGLKNYYLKKTISRSP

GK.

7. 4G9 Light Chain Sequences

Another embodiment provides an antibody or antigen binding fragment thereof having a light chain encoded by a nucleic acid with at least 50%, 60%, 70%, 80%, 85%, 90%, 95%, 99%, or 100% sequence identity to:

(SEQ ID NO: 32)

ATGGTATCCACACCTCAGTTCCTTGTATTTTTGCTTTTCTGGATTCCAGCCTCCAGAGGTGACATCT

TGCTGACTCAGTCTCCAGCCATCCTGTCTGTGAGTCCAGGAGAAAGAGTCAGTTTCTCCTGCAGGGC

CAGTCAGAGCATTGGCACAAGCATACACTGGTATCAGCAAAGAACAAATGGTTCTCCAAGGCTTCTC

ATAAAGTATGCTTCTGAGTCTATCTCTGGGATCCCTTCCAGGTTTAGTGGCAGTGGATCAGGGACAG

ATTTTACTCTTAGCATCAACAGTGTGGAGTCTGAAGATATTGCAGATTATTACTGTCAACAAAGTAA

TAGCTGGCCGTACACGTTCGGAGGGGGGACCAAGCTGGAAATAAAACGGGCTGATGCTGCACCAACT

GTATCCATCTTCCCACCATCCAGTGAGCAGTTAACATCTGGAGGTGCCTCAGTCGTGTGCTTCTTGA

ACAACTTCTACCCCAAAGACATCAATGTCAAGTGGAAGATTGATGGCAGTGAACGACAAAATGGCGT

CCTGAACAGTTGGACTGATCAGGACAGCAAAGACAGCACCTACAGCATGAGCAGCACCCTCACGTTG

ACCAAGGACGAGTATGAACGACATAACAGCTATACCTGTGAGGCCACTCACAAGACATCAACTTCAC

CCATTGTCAAGAGCTTCAACAGGAATGAGTGTTAG.

Dashed underline represents the leader sequence. Single underline represents the CDRs. Double underline represents the constant region.

The nucleic acid can be in a vector, for example an expression vector. The nucleic acid can be extrachromosal on inserted into a chromosome of a host cell, for example a Chinese Hamster Ovary cell.

Another embodiment provides an antibody or antigen binding fragment thereof having a light chain having an amino acid sequence with at least 50%, 60%, 70%, 80%, 85%, 90%, 95%, 99%, or 100% sequence identity to:

(SEQ ID NO: 33)
MVSTPQFLVFLLFWIPASRGDILLTQSPAILSVSPGERVSFSCRASQSIGTSIHWYQQRTNGSPRLLIKYASESI

SGIPSRFSGSGSGTDFTLSINSVESEDIADYYCQQSNSWPYTFGGGTKLEIKRADAAPTVSIFPPSSEQLTSGG

ASVVCFLNNFYPKDINVKWKIDGSERQNGVLNSWTDQDSKDSTYSMSSTLTLTKDEYERHNSYTCEATHK

TSTSPIVKSFNRNEC.

Underline represents the leader sequence. Double underline represents CDRs. Dashed underline represents the constant region.

Another embodiment provides an antibody or antigen binding fragment thereof having a light chain without the leader sequence having an amino acid sequence with at least 50%, 60%, 70%, 80%, 85%, 90%, 95%, 99%, or 100% sequence identity to:

(SEQ ID NO: 34)
DILLTQSPAILSVSPGERVSFSCRASQSIGTSIHWYQQRTNGSPRLLIKYASESISGIPSRFSGSGSGTDFTLSINS

VESEDIADYYCQQSNSWPYTFGGGTKLEIKRADAAPTVSIFPPSSEQLTSGGASVVCFLNNFYPKDINVKWK

IDGSERQNGVLNSWTDQDSKDSTYSMSSTLTLTKDEYERHNSYTCEATHKTSTSPIVKSFNRNEC.

Double underline represents CDRs. Dashed underline represents the constant region.

The amino acid sequence for CDR1 of the 4G9 light chain is RASQSIGTSIH (SEQ ID NO:35).

The amino acid sequence for CDR2 of the 4G9 light chain is YASESIS (SEQ ID NO:36).

The amino acid sequence for CDR3 of the 4G9 light chain is QQSNSWPYT (SEQ ID NO:37).

One embodiment provides a 4G9 antibody or antigen binding fragment thereof having a light chain with at least 50%, 60%, 70%, 80%, 85%, 90%, 95%, 99%, or 100% sequence identity to SEQ ID NO:33 or 34.

Another embodiment provides a 4G9 antibody or antigen binding fragment thereof having a light chain encoded by a nucleic acid with at least 50%, 60%, 70%, 80%, 85%, 90%, 95%, 99%, or 100% sequence identity to SEQ ID NO:32.

One embodiment provides a 4G9 antibody having three different CDRs selected from the group consisting of SEQ ID NO:35, 36, and 37.

Another embodiment provides an antibody or antigen binding fragment thereof having a heavy chain with an amino acid sequence having at least 50%, 60%, 70%, 80%, 85%, 90%, 95%, 99%, or 100% sequence identity to SEQ ID NO:27 or 28 and light chain with an amino acid sequence at least 50%, 60%, 70%, 80%, 85%, 90%, 95%, 99%, or 100% sequence identity to SEQ ID NO:33 or 34 or light and heavy chain combinations thereof.

Another embodiment provides a 4G9 antibody or antigen binding fragment thereof having three different heavy chain CDRs with an amino acid selected from the group consisting of SEQ ID NOs:29, 30, and 31 and three different light chain CDRs with amino acids selected from the group consisting of SEQ ID NOs:35, 36, and 37.

D. PD-1 Activating Epitope

Epitope-specific PD-1 binding moieties are disclosed herein. In one embodiment, the disclosed binding moieties immunospecifically bind to PD-1, and activate PD-1 mediated signal transduction.

The disclosed PD-1 epitope is formed by amino acids 96-110 of SEQ ID NO:1 and has an amino acid sequence as follows,

TYLCGAISLAPKAQI. (SEQ ID NO: 38)

1. Antibodies

One embodiment provides an antibody or epitope binding fragment thereof that immunospecifically binds to SEQ ID NO:38 on the surface of an immune cell and activates the immune cell. In one embodiment, the preferred immune cell is a T cell, more specifically a $CD8^+$ T cell. In another embodiment, the antibody or epitope binding fragment thereof immunospecifically binds SEQ ID NO:38 of PD-1 on the surface of an immune cell and promotes or induces an activating signal through PD-1 to activate the immune cell.

The epitope specific antibody can be a monoclonal antibody, a humanized antibody, a human antibody, a mouse antibody, a chimeric antibody, or a fragment thereof. Exemplary antibodies and methods of their production are discussed below.

2. Fusion Protein

In one embodiment, the epitope-specific PD-1 binding moiety is a fusion protein. All of part of one or more of the disclosed PD-1 epitope antibodies or epitope binding fragments above can be coupled to other polypeptides to form fusion proteins. Fusion polypeptides have a first fusion partner including all or a part of one or more of the disclosed PD-1 epitope antibodies or epitope binding fragments fused to a second polypeptide directly or via a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (first polypeptide or second polypeptide) of the fusion protein. Similarly, the domain that functions to dimerize or multimerize the fusion proteins can either be a separate domain, or alternatively can be contained within one of the other domains (first polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

$$N—R_1—R_2—R_3—C$$

wherein "N" represents the N-terminus of the fusion protein, "C" represents the C-terminus of the fusion protein, "$R_1$" is all or part of one of the disclosed PD-1 epitope antibodies or epitope binding fragments, or functional variant or fragment thereof, "$R_2$" is an optional peptide/polypeptide linker domain, and "$R_3$" is a second polypeptide. Alternatively, $R_3$ is all or part of one of the disclosed PD-1 epitope antibodies or epitope binding fragments, or functional variant or fragment thereof and $R_1$ is the second polypeptide.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

3. Aptamers

In some embodiments, the epitope-specific binding moiety is an aptamer. Aptamers are molecules that interact with a target molecule, preferably in a specific way. In one embodiment, the aptamer binds to SEQ ID NO:38 on the surface of an immune cell and promotes or induces an activating signal through PD-1 to activate the immune cell. Typically aptamers are small nucleic acids ranging from 15-50 bases in length that fold into defined secondary and tertiary structures, such as stem-loops or G-quartets. Aptamers can bind to protein, cells, small organic molecules, or peptides. Aptamers can bind small molecules, such as ATP and theophiline, as well as large molecules, such as reverse transcriptase and thrombin. Aptamers can bind very tightly with Kd's from the target molecule of less than 10-12 M. It is preferred that the aptamers bind the target molecule with a Kd less than 10-6, 10-8, 10-10, or 10-12. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a Kd with the target molecule at least 10, 100, 1000, 10,000, or 100,000 fold lower than the Kd with a background binding molecule. It is preferred when doing the comparison for a polypeptide for example, that the background molecule be a different polypeptide. Representative examples of how to make and use aptamers to bind a variety of different target molecules are known in the art.

4. Small Molecules

In some embodiments, the epitope-specific binding moiety can be a small molecule. The term "small molecule" generally refers to small organic compounds having a molecular weight of more than about 100 and less than about 2,500 Daltons, preferably between 100 and 2000, more preferably between about 100 and about 1250, more preferably between about 100 and about 1000, more preferably between about 100 and about 750, more preferably between about 200 and about 500 Daltons. Small molecule agonists of the activating epitope of PD-1 can be identified using routine screening methods. In some embodiments, the screening assay can include random screening of large libraries of test compounds. Assays can include determinations of PD-1 induced immune response or activation of T cells.

E. Pharmaceutical Compositions

Pharmaceutical compositions including the disclosed antibodies and antigen binding fragments thereof are provided. Pharmaceutical compositions containing the antibodies and antigen binding fragments thereof can be for administration by parenteral (intramuscular, intraperitoneal, intravenous (IV) or subcutaneous injection).

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed antibodies and antigen binding fragments thereof, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed antibodies and antigen binding fragments thereof, generally dosage levels of 0.001 to 20 mg/kg of body weight daily are administered to mammals. Generally, for intravenous injection or infusion, dosage may be lower.

In certain embodiments, the antibodies and antigen binding fragments thereof are administered locally, for example by injection directly into a site to be treated. Typically, the injection causes an increased localized concentration of the immunomodulatory agent composition which is greater than that which can be achieved by systemic administration. The immunomodulatory agent compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, the compositions containing the disclosed antibodies and antigen binding fragments are administered in an aqueous solution, by parenteral injection. The formulation may also be in the form of a suspension or emulsion. In general, pharmaceutical compositions are provided including effective amounts of an antibody or antigen binding fragment thereof, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In some embodiments the antibody compositions are formulated for oral delivery. The oral dosage forms of antibodies resist proteolysis and can deliver a greater fraction of immunoreactive antibody locally in the gastrointestinal tract for the treatment of infections or allow the absorption of antibodies for the treatment or prevention of systemic conditions (Reilly, R M, et al. Clin Pharmacokinet., 32(4):313-23 (1997); Victoria S Jasion and Bruce P Burnett, Nutr J.; 14: 22 (2015); and Philippart, M., et al., Drug Res (Stuttg) 66(03):113-120 (2016)).

Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013, 556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The antibodies and antigen binding fragments thereof can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

For oral formulations, the location of release may be the stomach, the small intestine (the duodenum, the jejunem, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Controlled Delivery Polymeric Matrices

The antibodies and antigen binding fragments thereof disclosed herein can also be administered in controlled release formulations. The antibodies and antigen binding fragments thereof can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the antibody or antigen binding fragment thereof is enclosed in a semipermeable membrane which allows water to enter and push drug out through a single small opening due to osmotic effects.

Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be cross-linked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Manufacture

A. Methods of Making Antibodies

The disclosed antibodies can be generated in cell culture, in phage, or in various animals, including but not limited to cows, rabbits, goats, mice, rats, hamsters, guinea pigs, sheep, dogs, cats, monkeys, chimpanzees, apes. In one embodiment, the various animals can be transgenic animals genetically engineered to produce human or humanized antibodies. Therefore, in one embodiment, the antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition).

The disclosed antibodies can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to proteins, polypeptides. See, e.g., *Antibody Engineering: A Practical Approach* (Oxford University Press, 1996).

For example, suitable antibodies with the desired biologic activities can be identified using in vitro assays including but not limited to: proliferation, migration, adhesion, soft agar growth, angiogenesis, cell-cell communication, apoptosis, transport, signal transduction, and in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies based on the disclosed antibodies and antigen binding fragments thereof. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

One embodiment provides divalent single-chain variable fragments (di-scFvs) that can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Another embodiment provides a monoclonal antibody obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The disclosed antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

B. Methods for Producing Isolated Nucleic Acid Molecules

One embodiment provides nucleic acids encoding the disclosed antibodies or antigen binding fragments thereof. The nucleic acids can encode the entire antibody or antigen binding fragments thereof or a light chain, heavy chain, combinations thereof or CDRs thereof.

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Protein-encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992.

IV. Methods of Use

The disclosed antibodies and antigen binding fragments thereof can be used to modulate an immune response in a subject in need thereof. One embodiment provides a method of activating immune cells expressing PD-1, for example T cells, to proliferate or enhance the biological activity of the immune cells expressing PD-1 by administering the disclosed antibodies and antigen fragments thereof, optionally including a second therapeutic agent.

A. Immune Response Stimulation

1. Therapeutic Strategies

Methods of inducing or enhancing an immune response in a subject are provided. Typically, the methods include administering a subject an effective amount of one or more of the disclosed antibodies and antigen binding fragments thereof to immunospecifically bind to PD-1 and induce, promote, or enhance a stimulatory or activating signal through PD-1 to activate the immune cell. The immune response can be, for example inducing, promoting or enhancing T cell activation, secretion of cytokines by immune cells, T cell proliferation. The disclosed antibodies or antigen binding fragments thereof can be administered to a subject in need thereof in an effective amount to overcome T cell exhaustion and/or T cell anergy. Overcoming T cell exhaustion or T cell anergy can be determined by measuring T cell function using known techniques.

The methods can be used in vivo or ex vivo to induce, promote, or enhance a stimulating immune response.

In some embodiments, the antibody or antigen binding fragment thereof, or nucleic acid encoding the antibody or antigen binding fragment thereof, is administered directly to the subject. In some embodiments, antibody or antigen binding fragment thereof is contacted with cells (e.g., immune cells) ex vivo, and the treat cells are administered to the subject (e.g., adoptive transfer). The antibody or antigen binding fragment thereof can enable a more robust immune response to be possible. The disclosed compositions are useful to stimulate or enhance immune responses involving T cells causing an activating signal through PD-1 on immune cells.

2. Subjects to be Treated a. Treatment of Cancer

The disclosed antibodies and compositions thereof and methods can be used to treat cancer. Generally, the agents are used to stimulate or enhance an immune response to cancer in the subject by administering to the subject an amount of a disclosed antibody or antigen binding fragment thereof that induces, promotes, or enhances an activating signal through PD-1. The method can reduce one or more symptoms of the cancer.

The immune cells activated by the disclosed antibodies or fragments thereof can kill cancer cells and reduce tumor burden in a subject. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and antibody compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

b. Treatment of Infections

The disclosed antibody compositions and methods can be used to treat infections and infectious diseases. Generally, the agents are used to stimulate or enhance an immune response to an infection in the subject by administering to the subject an amount of one or more of the disclosed antibodies or antigen binding fragments thereof that sends a activating or stimulating signal through PD-1. The method can reduce one or more symptoms of the infection.

The infection or disease can be caused by a bacterium, virus, protozoan, helminth, or other microbial pathogen that enters intracellularly and is attacked, i.e., by cytotoxic T lymphocytes.

The infection or disease can be acute or chronic. An acute infection is typically an infection of short duration. During an acute microbial infection, immune cells begin expressing immunomodulatory receptors. Accordingly, in some embodiments, the method includes increasing an immune stimulatory response against an acute infection.

The infection can be caused by, for example, but not limited to *Candida albicans, Listeria monocytogenes, Streptococcus pyogenes, Streptococcus pneumoniae, Neisseria meningitidis, Staphylococcus aureus, Escherichia coli, Acinetobacter baumannii, Pseudomonas aeruginosa* or *Mycobacterium*.

In some embodiments, the disclosed antibody compositions are used to treat chronic infections, for example infections in which T cell exhaustion or T cell anergy has occurred causing the infection to remain with the host over a prolonged period of time.

Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus.

Because viral infections are cleared primarily by T cells, an increase in T-cell activity would be therapeutically useful in situations where more rapid or thorough clearance of an infective viral agent would be beneficial to an animal or human subject. Thus, the disclosed compositions can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) and other viral infections, caused by, for example, HTLV, hepatitis virus, respiratory syncytial virus, vaccinia virus, and rabies virus. The molecules can be administered topically to treat viral skin diseases such as herpes lesions or shingles, or genital warts. The molecules can also be administered systemically to treat systemic viral diseases, including, but not limited to, AIDS, influenza, the common cold, or encephalitis.

Representative infections that can be treated, include but are not limited to infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*.

Other microorganisms that can be treated using the disclosed compositions and methods include, bacteria, such as those of *Klebsiella, Serratia, Pasteurella*; pathogens associated with cholera, tetanus, botulism, anthrax, plague, and Lyme disease; or fungal or parasitic pathogens, such as *Candida (albicans, krusei, glabrata, tropicalis,* etc.*), Cryptococcus, Aspergillus (fumigatus, niger,* etc.*),* Genus *Mucorales (mucor, absidia, rhizophus), Sporothrix (schenkii), Blastomyces (dermatitidis), Paracoccidioides (brasiliensis), Coccidioides (immitis)* and *Histoplasma (capsulatuma), Entamoeba, histolytica, Balantidium coli, Naegleria fowleri, Acanthamoeba* sp., *Giardia Zambia, Cryptosporidium* sp., *Pneumocystis carinii, Plasmodium vivax, Babesia microti, Trypanosoma brucei, Trypanosoma cruzi, Toxoplasma gondi,* etc.*), Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia,* or *Trypanosoma,* etc.

V. Combination Therapies for Increasing Immune Responses

The disclosed antibodies and antigen binding fragments thereof and compositions thereof can be administered to a subject in need thereof either alone or in combination with one or more additional therapeutic agents. In some embodiments, the antibodies and antigen binding fragments thereof and the additional therapeutic agent are administered separately, but simultaneously. The antibodies and antigen binding fragments thereof and the additional therapeutic agent can also be administered as part of the same composition. In other embodiments, the antibodies and antigen binding fragments thereof and the second therapeutic agent are administered separately and at different times, but as part of the same treatment regime. The additional therapeutic agents can be administered before, after, or in alternation with the administration of the disclosed antibodies and antigen binding fragments thereof.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The antibodies and antigen binding fragments thereof can be the first or the second therapeutic agent.

The antibodies and antigen binding fragments thereof and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary additional therapeutic agents include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the immunomodulatory agent can be co-administered with one or more additional agents that function to enhance or promote an immune response or reduce or inhibit an immune response.

A. Antimicrobials

In one embodiment, the antibodies and antigen binding fragments thereof can be administered to the subject in combination with an antimicrobial such as an antibiotic, an antifungal, an antiviral, an anti-parasitics, or essential oil. In another embodiment, the disclosed antibodies and antigen binding fragments thereof can be used in a preventive or prophylactic role in the treatment and prevention of disease, and also in the context of severe trauma injuries like major burn, open bone fracture, accidental amputation or other wounds.

In some embodiments, the subject is administered the antibodies and antigen binding fragments thereof and/or the antimicrobial at time of admission to the hospital to prevent further bacterial, fungal or viral complications. The antibiotic can target pathogens and the antibodies and antigen binding fragments thereof can stimulate the immune system to provide an enhanced response to treat or prevent further infection or disease.

1. Chemotherapeutic Agents

The antibodies and antigen binding fragments thereof can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

2. Other Immunomodulators a. PD-1 Antagonists

In some embodiments, the antibodies and antigen binding fragments thereof are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U.S.A*, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos.: 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., *Clin. Cancer Res.,* 14:30443051 (2008).

Exemplary anti-PD-L1 antibodies include, but are not limited to, those described in the following U.S. Pat. Nos. 8,383,796, 9,102,725, 9,273,135, 9,393,301, and 9,580,507 all of which are specifically incorporated by reference herein in their entirety.

For anti-B7-DC (also referred to as anti-PD-L2) antibodies see U.S. Pat. Nos.: 7,411,051, 7,052,694, 7,390,888, 8,188,238, and 9,255,147.

Other exemplary PD-1 receptor antagonists include, but are not limited to PD-L2 polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian PD-L1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as PD-L1 or B7-DC, and prevent binding to the endogenous PD-1 receptor, thereby preventing inhibitory signal transduction. PD-L1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., PNAS, 105:10483-10488 (2008)). B7-1 or soluble fragments thereof, which can bind to the PD-L1 ligand and prevent binding to the endogenous PD-1 receptor, thereby preventing inhibitory signal transduction, are also useful.

PD-1 and PD-L1 anti-sense nucleic acids, both DNA and RNA, as well as siRNA molecules can also be PD-1 antagonists. Such anti-sense molecules prevent expression of PD-1 on T cells as well as production of T cell ligands, such as PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., *Clinical Kidney Journal*, 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.*, 277:7363-7368 (2002). Such small organics could be administered alone or together with an anti-CTLA4 antibody to reduce inhibitory signal transduction of T cells.

3. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(-)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

In one embodiment low doses of CTX are used in combination with the disclosed antibodies and antigen binding fragments thereof. Low doses of CTX (<200 mg/kg) can have immune stimulatory effects, including stimulation of anti-tumor immune responses in humans and mouse models of cancer (Brode & Cooke *Crit Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

In one embodiment, the optimal dose for CTX to potentiate an anti-tumor immune response, is one that lowers overall T cell counts by lowering Treg levels below the normal range but is subtherapeutic (see Machiels et al. Cancer Res. 61:3689-3697 (2001)).

In some embodiments, CTX is used as an immunopotentiating agent at a dose of 300 mg/m$^2$. In another embodiment, for an average male (6 ft, 170 pound (78 kg) with a body surface area of 1.98 m$^2$), 300 mg/m$^2$, the dose of CTX is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

VI. Transgenic Animals

One embodiment provides a transgenic animal that produces antibodies or antigen binding fragments thereof having heavy chain CDRs with an amino acid sequences according to SEQ ID NOs:6, 7, and 8 and light chain CDRs with amino acids according to SEQ ID NOs: 12, 13, and 14. In one embodiment, the transgenic animal is a rodent, for example a mouse.

Another embodiment provides a transgenic animal that produces antibodies or antigen binding fragments thereof having heavy chain CDRs with an amino acid sequences according to SEQ ID NO:18, 19, and 20 and three different light chain CDRs with amino acids selected from the group consisting of SEQ ID NOs: 24, 13, and 25. In one embodiment, the transgenic animal is a rodent, for example a mouse.

Another embodiment provides a transgenic animal that produces antibodies or antigen binding fragments thereof having heavy chain CDRs with an amino acid sequences according to SEQ ID NOs: 29, 30, and 31 and light chain CDRs with amino acids according to SEQ ID NOs: 35, 36, and 37. In one embodiment, the transgenic animal is a rodent, for example a mouse.

Methods of making transgenic animals that produce antibodies are known in the art. See for example A. Jakobovits, Curr Opin Biotechnol.,6(5):561-6 (1995) and Bruggemann, M., et al., Arch Immunol Ther Exp (Warsz)., 63(2):101-108 (2015); Jakobovits, A., et al., "From XenoMouse technology to panitumumab, the first fully human antibody product from transgenic mice." Nat Biotechnol. 25(10):1134-43 (2007); Lonberg N. (2005) "Human antibodies from transgenic animals." Nat Biotechnol. 23(9):1117-25 and U.S. Pat. Nos. 9,708,635; 9,686,970; 9,499,838; 9,445,581; 9,388,446; 8,835,712; 8,703,485; 8,232,449; 7,795,494; and 5,939,598.

EXAMPLES

Example 1: Anti-PD-1 Antibody Production

Results

Production of anti-PD-1 antibodies produced clones 4G9, 4C12, and 5C2 which were selected for characterization.

Example 2: Interaction Kinetics Between Anti-PD-1 Antibodies and PD-1

Materials and Methods

Antibodies from clones 4G9, 4C12, and 5C2 where characterized using a Biocore™ system available from GE. The analyte was mouse or human PD-1 and the ligand was the anti-PD-1 antibody. Analyte concentrations were 0, 62.5, 125, 250, 500, and 1000 nM where indicated.

Results

FIG. 1 and Table 1 show interaction analysis of 4G9 with human PD-1. The equilibrium association constant ($K_A$) was $9.52 \times 10^5$ (1/M). The equilibrium dissociation constant ($K_D$) was $1.05 \times 10^{-6}$ (M).

TABLE 1

Interaction analysis of 4G9 with human PD-1.

| Ligand | Analyte | Ka (1/Ms) | Kd (1/s) | Rmax | KA (1/M) | KD (M) | Conc (Nm) | Chi$^2$ |
|---|---|---|---|---|---|---|---|---|
| 4G9 580 RU | Human PD-1 | NA | NA | 15.1 | $9.52 \times 10^5$ | $1.05 \times 10^{-6}$ | 0<br>125<br>250<br>500<br>500<br>1000 | 0.464 |

Figure 2:
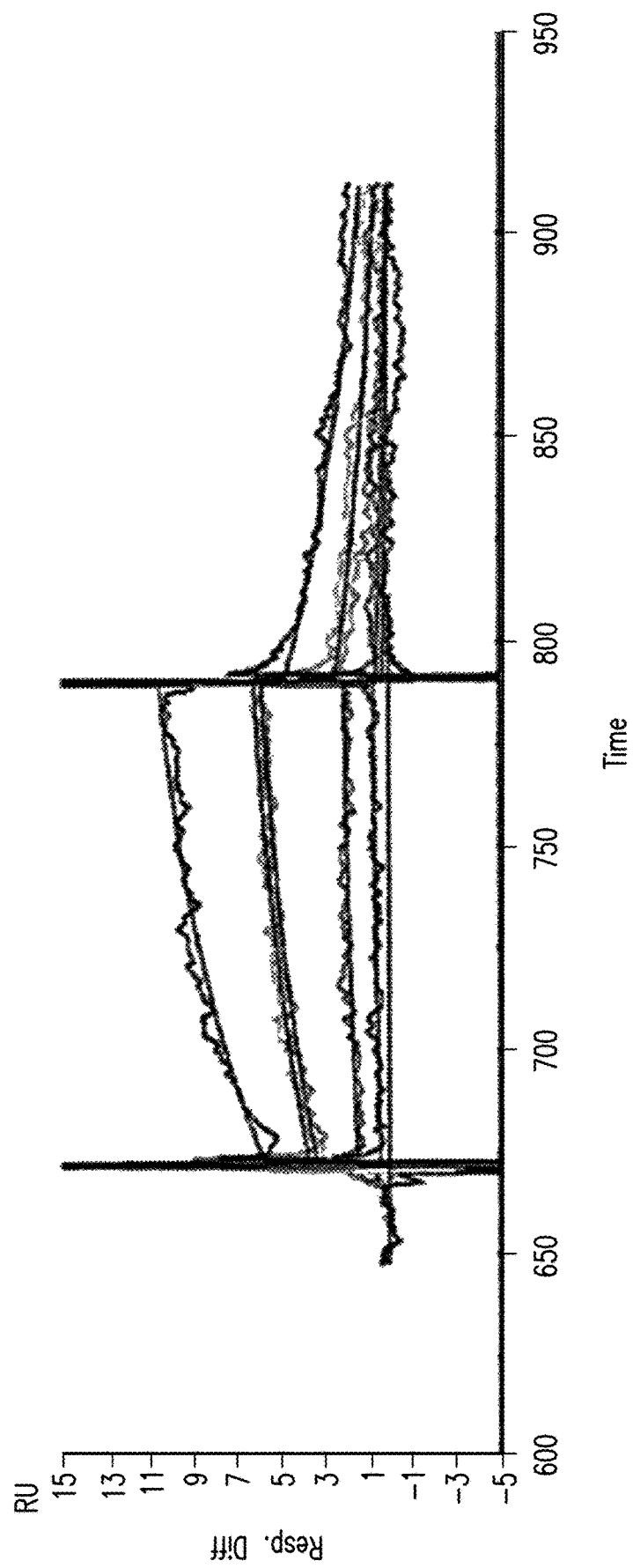
FIG. 2 is a graph showing the interaction kinetics as a function of time between monoclonal antibody 4G9 and mouse PD-1. The graph shows traces from concentrations of mouse PD-1 at 0, 62.5, 125, 500, 500, and 1000 nM.

FIG. 2 and Table 2 show interaction analysis of 4G9 with mouse PD-1. The equilibrium association constant ($K_A$) was $1.94 \times 10^5$ (1/M). The equilibrium dissociation constant ($K_D$) was $5.15 \times 10^{-6}$ (M).

TABLE 2

Interaction analysis of 4G9 with mouse PD-1.

| Ligand | Analyte | Ka (1/Ms) | Kd (1/s) | Rmax | KA (1/M) | KD (M) | Conc (Nm) | Chi$^2$ |
|---|---|---|---|---|---|---|---|---|
| 4G9 580 RU | Mouse PD-1 | $2.00 \times 10^3$ | 0.0103 | 38.8 | $1.94 \times 10^5$ | $5.15 \times 10^{-6}$ | 0<br>125<br>250<br>500<br>500<br>1000 | 0.112 |

Figure 3:
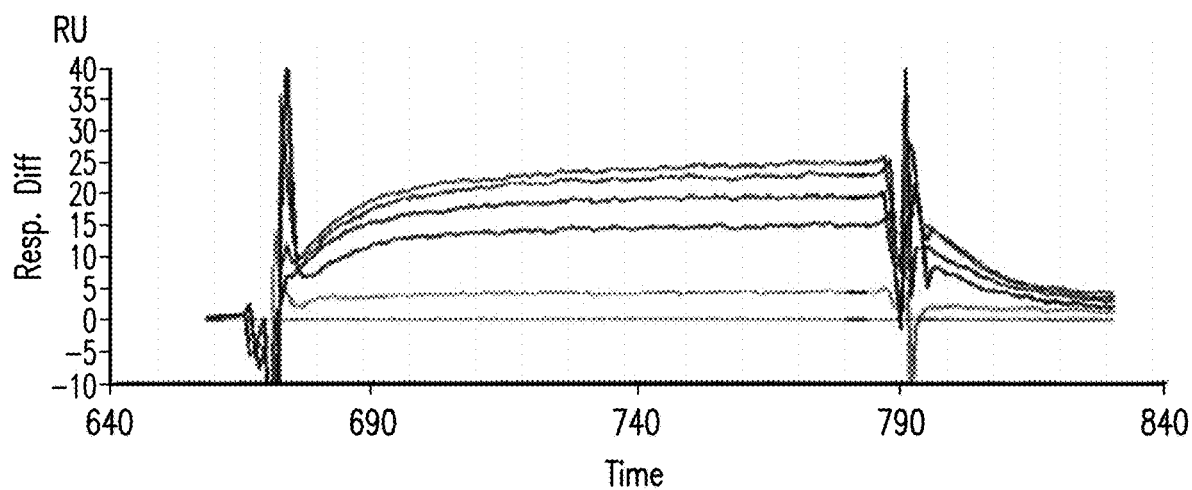
FIG. 3 is a graph showing the interaction kinetics as a function of time between monoclonal antibody 4C12 and human PD-1. The graph shows traces from concentrations of human PD-1 at 0, 125, 250, 500, 500, and 1000 nM.

FIG. 3 and Table 3 show interaction analysis of 4C12 with human PD-1. The equilibrium association constant ($K_A$) was $3.14 \times 10^6$ (1/M). The equilibrium dissociation constant ($K_D$) was $3.19 \times 10^{-7}$ (M).

TABLE 3

Interaction analysis of 4C12 with human PD-1.

| Ligand | Analyte | Ka (1/Ms) | Kd (1/s) | Rmax | KA (1/M) | KD (M) | Conc (Nm) | Chi$^2$ |
|---|---|---|---|---|---|---|---|---|
| 4C12 425 RU | Human PD-1 | NA | NA | 33.9 | $3.14 \times 10^6$ | $3.19 \times 10^{-7}$ | 0<br>125<br>250<br>500<br>500<br>1000 | 2.33 |

Figure 4:
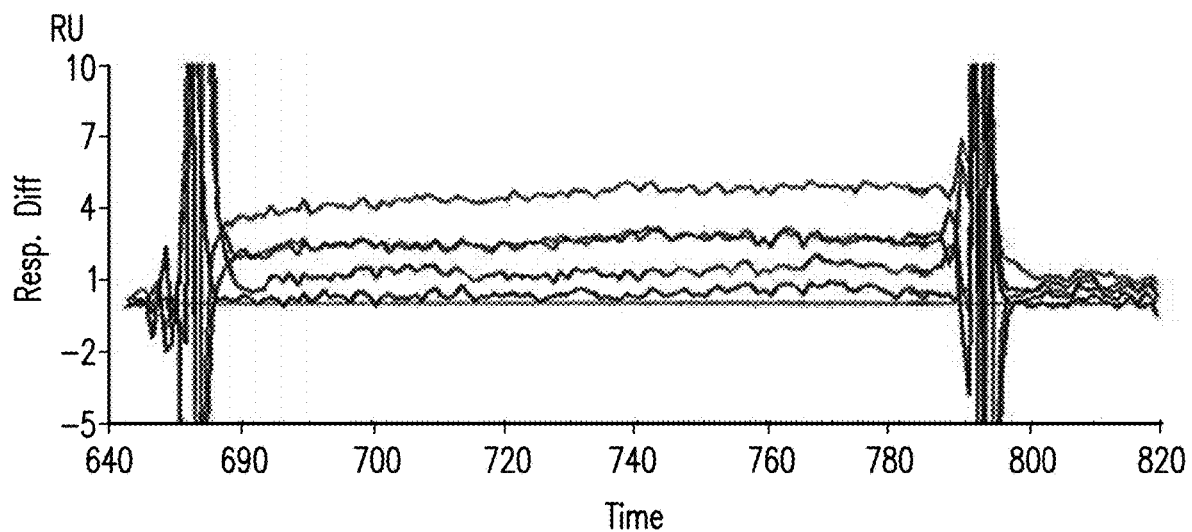
FIG. 4 is a graph showing the interaction kinetics as a function of time between monoclonal antibody 5C2 and human PD-1. The graph shows traces from concentrations of mouse PD-1 at 0 and 1000 nM.

FIG. 4 and Table 4 show interaction analysis of 5C2 with human PD-1. The equilibrium association constant ($K_A$) was $2.02 \times 10^5$ (1/M). The equilibrium dissociation constant ($K_D$) was $4.95 \times 10^{-6}$ (M).

TABLE 4

Interaction analysis of 5C2 with human PD-1.

| Ligand | Analyte | Ka (1/Ms) | Kd (1/s) | Rmax | KA (1/M) | KD (M) | Conc (Nm) | Chi$^2$ |
|---|---|---|---|---|---|---|---|---|
| 5C2 320 RU | Human PD-1 | NA | NA | 28.4 | $2.02 \times 10^5$ | $4.95 \times 10^{-6}$ | 0<br>125<br>250<br>500<br>500<br>1000 | 0.0263 |

Figure 5:
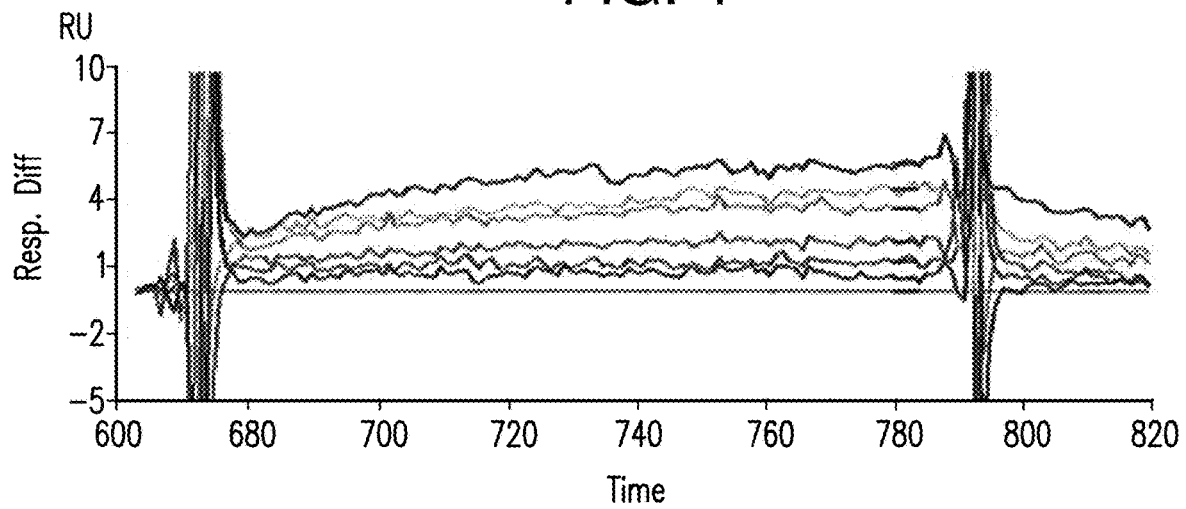
FIG. 5 is a graph showing the interaction kinetics as a function of time between monoclonal antibody 5C2 and mouse PD-1. The graph shows traces from concentrations of human PD-1 at 0, 62.5, 125, 250, 500, 500, and 1000 nM.

FIG. 5 and Table 5 show interaction analysis of 5C2 with mouse PD-1. The equilibrium association constant ($K_A$) was $1.18 \times 10^6$ (1/M). The equilibrium dissociation constant ($K_D$) was $8.50 \times 10^{-7}$ (M).

TABLE 5

Interaction analysis of 5C2 with mouse PD-1.

| Ligand | Analyte | Ka (1/Ms) | Kd (1/s) | Rmax | KA (1/M) | KD (M) | Conc (Nm) | Chi$^2$ |
|---|---|---|---|---|---|---|---|---|
| 5C2 320 RU | Mouse PD-1 | NA | NA | 11 | $1.18 \times 10^6$ | $8.50 \times 10^{-7}$ | 0<br>125<br>250<br>500<br>500<br>1000 | 0.107 |

Example 3: Binding of Anti-PD-1 Antibodies to EL4 Cells

Materials and Methods

Murine EL4 cells that constitutively express PD-1 were used in fluorescence activated cell sorter to evaluate binding of 4G9, 5C2, and 4C12 to the cells.

Results

Figure 6A:
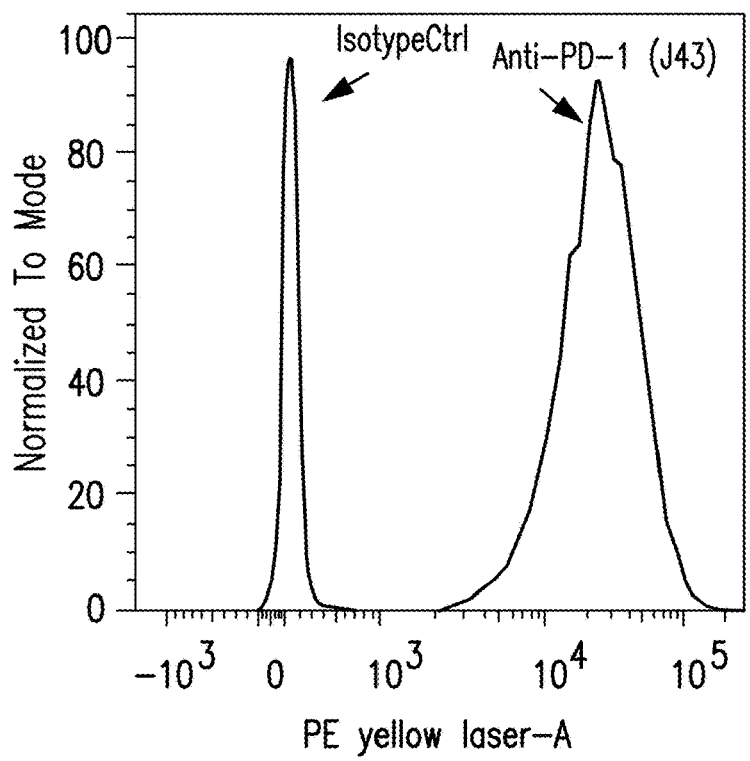
FIG. 6A is a flow cytometry histogram of EL4 cells stained with an isotype control antibody or commercial anti-PD-1 antibody J43.
Figure 6B:
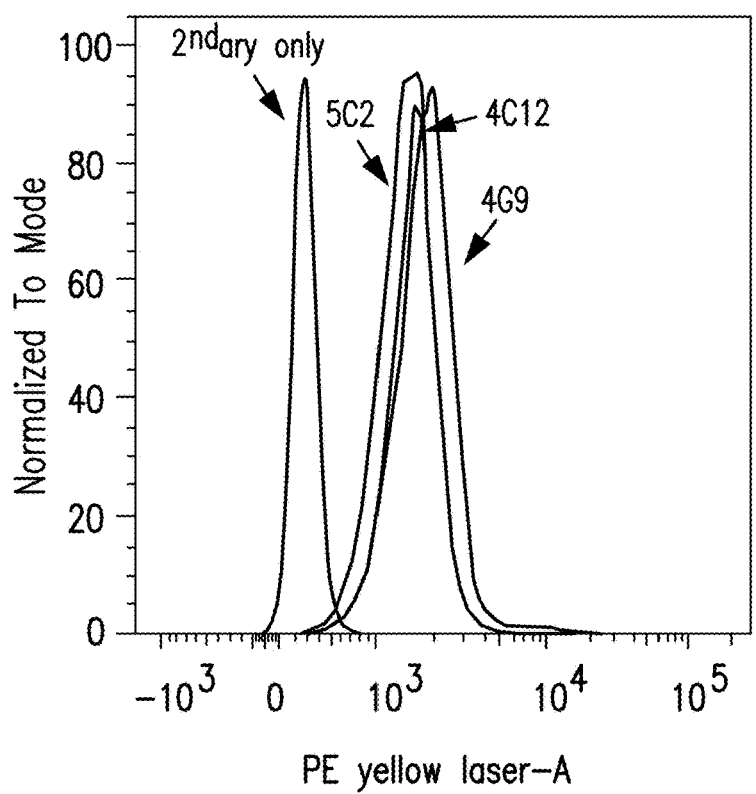
FIG. 6B is a flow cytometry histogram of EL4 cells stained with secondary antibody only or antibodies 4G9, 5C2, and 4C12.
Figure 6C:
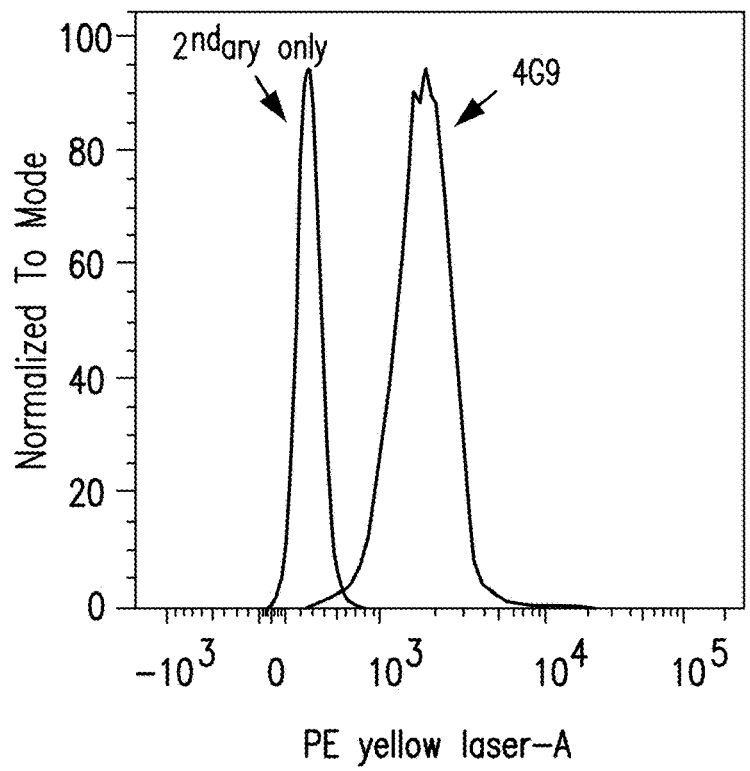
FIG. 6C is a flow cytometry histogram of El4 cells stained with secondary antibody only or antibody 4G9.
Figure 6D:
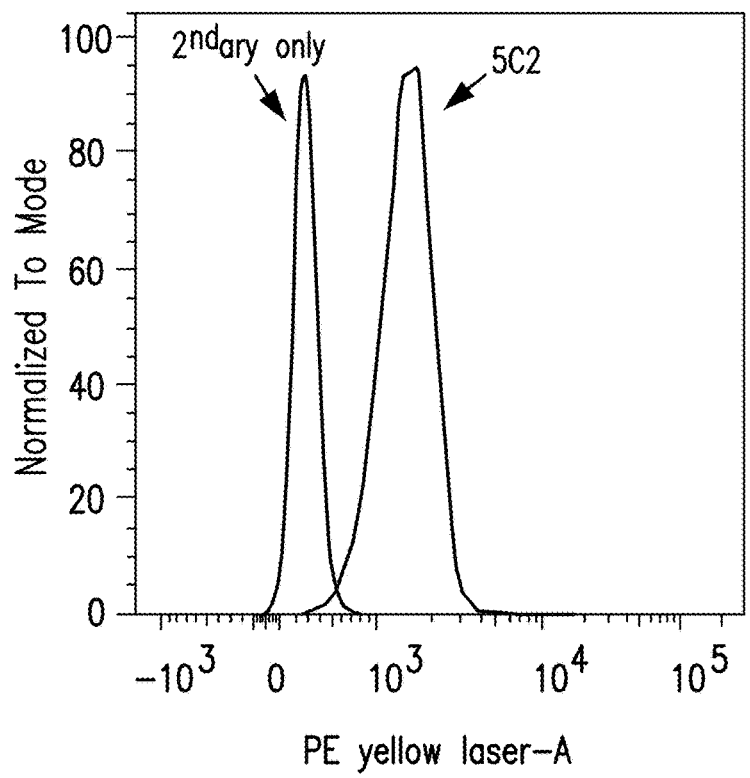
FIG. 6D is a flow cytometry histogram of El4 cells stained with secondary antibody only or antibody 5C2.
Figure 6E:
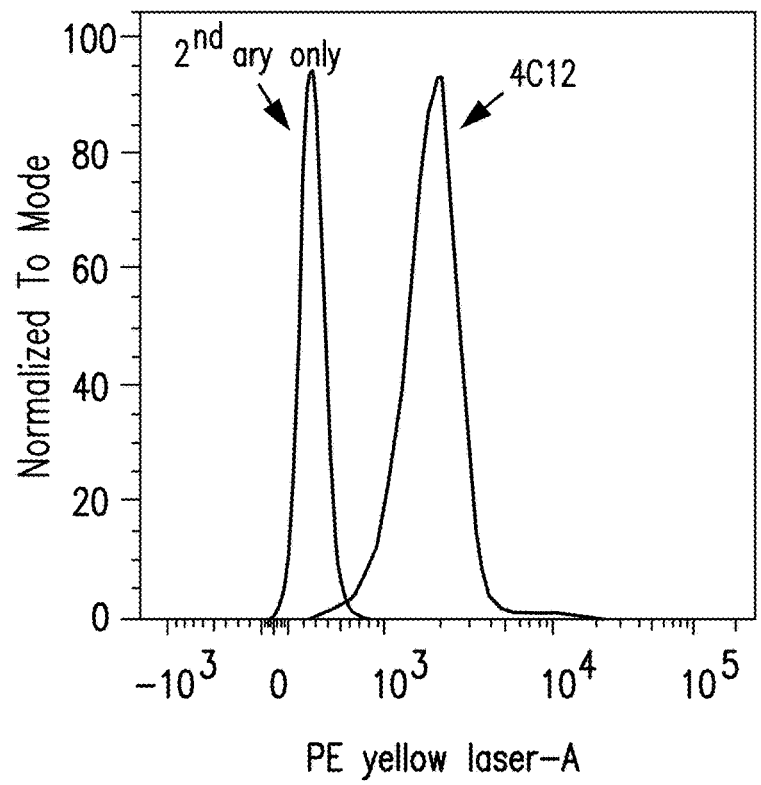
FIG. 6E is a flow cytometry histogram of El4 cells stained with secondary antibody only or antibody 4C12.
Figure 6F:
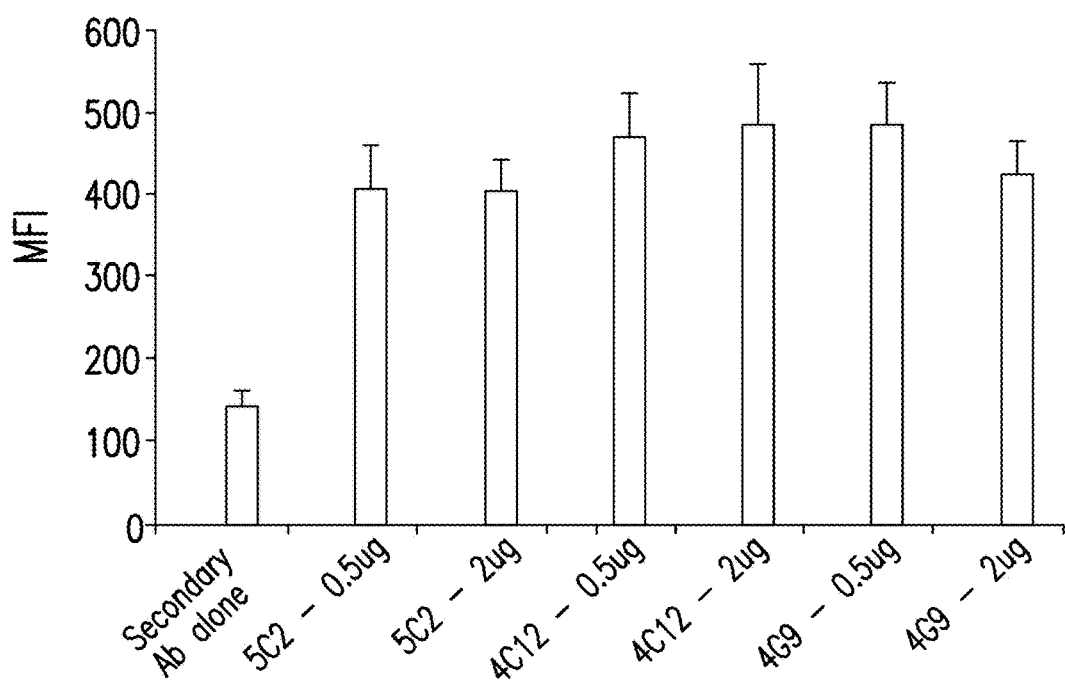
FIG. 6F is a bar graph showing binding of various purified mouse PD-1 antibodies to EL4 cells.

FIG. 6A is a flow cytometry histogram that shows commercial anti-PD-1 binds to EL4 cells and the control isotype antibody does not bind to EL4 cells. FIG. 6B is a flow cytometry histogram that shows that 4G9, 5C2, and 4C12 bind to EL4 cells and secondary antibody alone does not. FIG. 6C is a flow cytometry histogram that shows that 4G9 anti-PD-1 antibody binds to EL4 cells and secondary antibody alone does not. FIG. 6D is a flow cytometry histogram that shows that 5C2 anti-PD-1 antibody binds to EL4 cells and secondary antibody alone does not. FIG. 6E is a flow cytometry histogram that shows that 4C12 anti-PD-1 antibody binds to EL4 cells and secondary antibody alone does not.

Example 4: Agonistic Activity of Anti-PD-1 Antibodies

Materials and Methods

Mouse CD4 T Cells

Purified mouse CD4 T cells were stimulated with anti-CD3/anti-CD28 Ab for 48 hrs, then anti-PD-1 Abs (10 ug/ml) were added to culture along with Protein A beads for another 48 hrs. In some samples anti-PD-L1 Ab was added to block PD-1/PD-L1 interaction to dissect the agonist effect of test Abs. CBA assay was used to detect IFNγ and IL-2 concentrations in supernatants.

Human CD4 T Cells

Purified human CD4 T cells were stimulated with anti-CD3/anti-CD28 Ab for 48 hrs, then anti-PD-1 Abs (1 or 10 ug/ml) were added to culture along with Protein A beads for another 48 hrs. CBA assay was used to detect IFNγ concentrations in supernatants.

Results

Figure 7A:
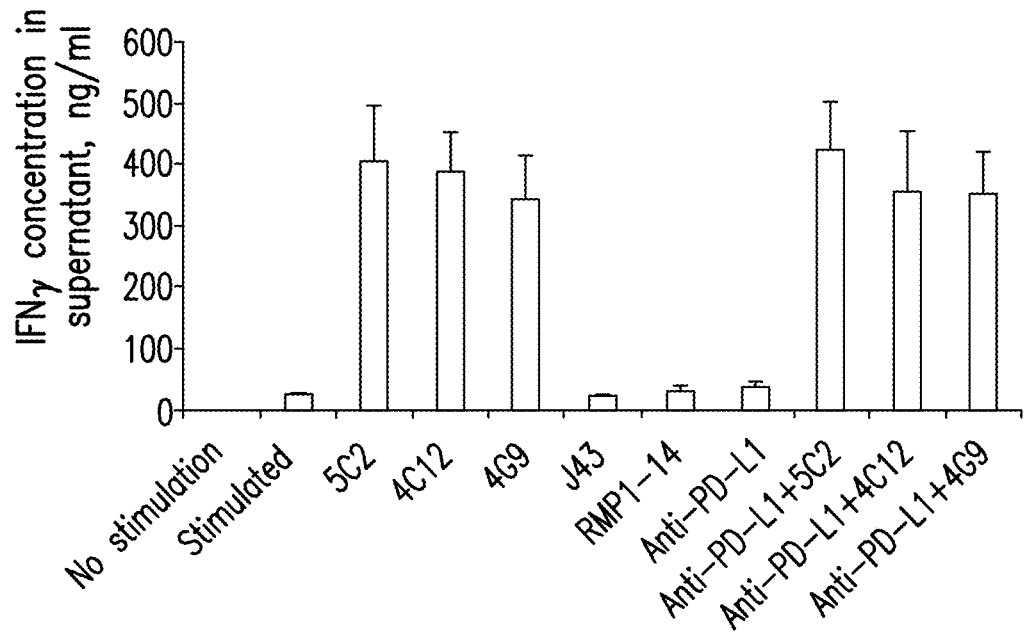
FIGS. 7A and 7B are bar graphs showing concentration of IFNγ (FIG. 7A) or IL-2 in supernatant from CD4 T cells treated with various antibodies. The X axis is treatment group and the Y axis is concentration (ng/ml).
Figure 7B:
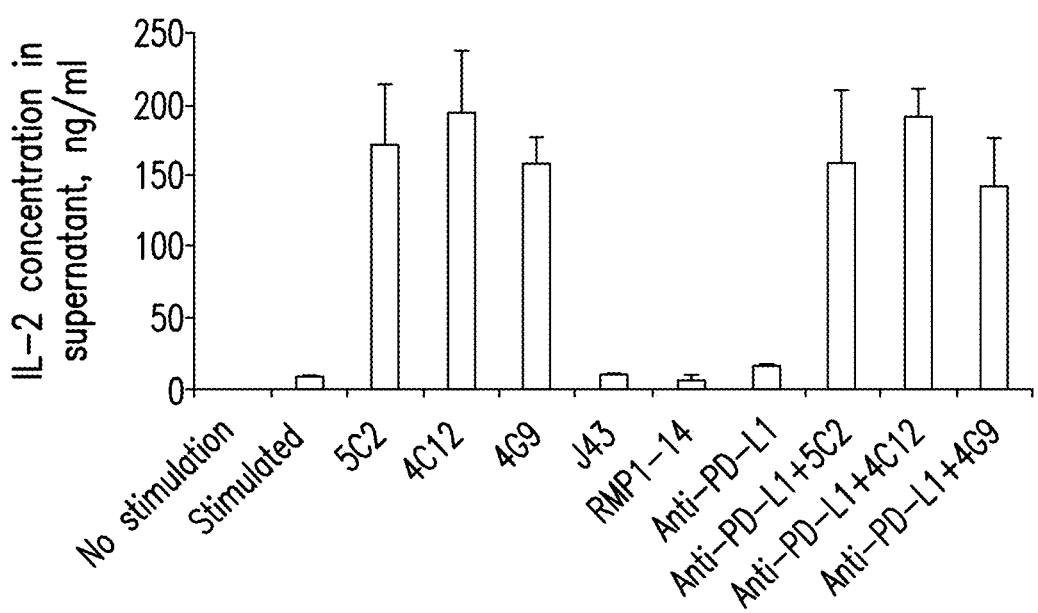
Figure 7C:
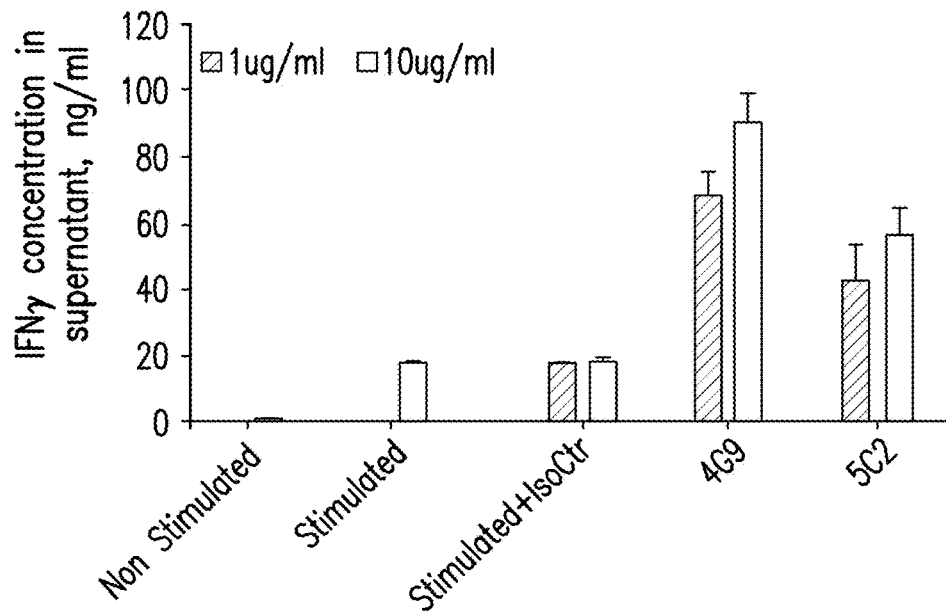
FIG. 7C is a bar graph showing IFNγ concentration in supernatant from human CD4 T cells treated with 4G9 or 5C2 antibodies. The X axis represents treatment group and the Y axis represents concentration (ng/mL).

FIGS. 7A and 7B show that stimulated CD4 T cells treated with anti-PD-1 antibodies 5C2, 4C12, and 4G9, had higher concentrations of IFNγ and IL-2 in supernatants compared to untreated cells or cells treated with anti-PD-L1 antibodies. FIG. 7C shows that stimulated human CD4 T cells treated with anti-PD-1 antibodies 4G9 and 5C2 had a higher concentration of IFNγ supernatant compared to untreated cells or cells treated with isotype control antibody.

Example 5: Hybridomas Enhance Akt Phosphorylation

Materials and Methods

Intracellular staining of pAKT (S473) was used as a marker for T cell activation.

Results

Figure 8:
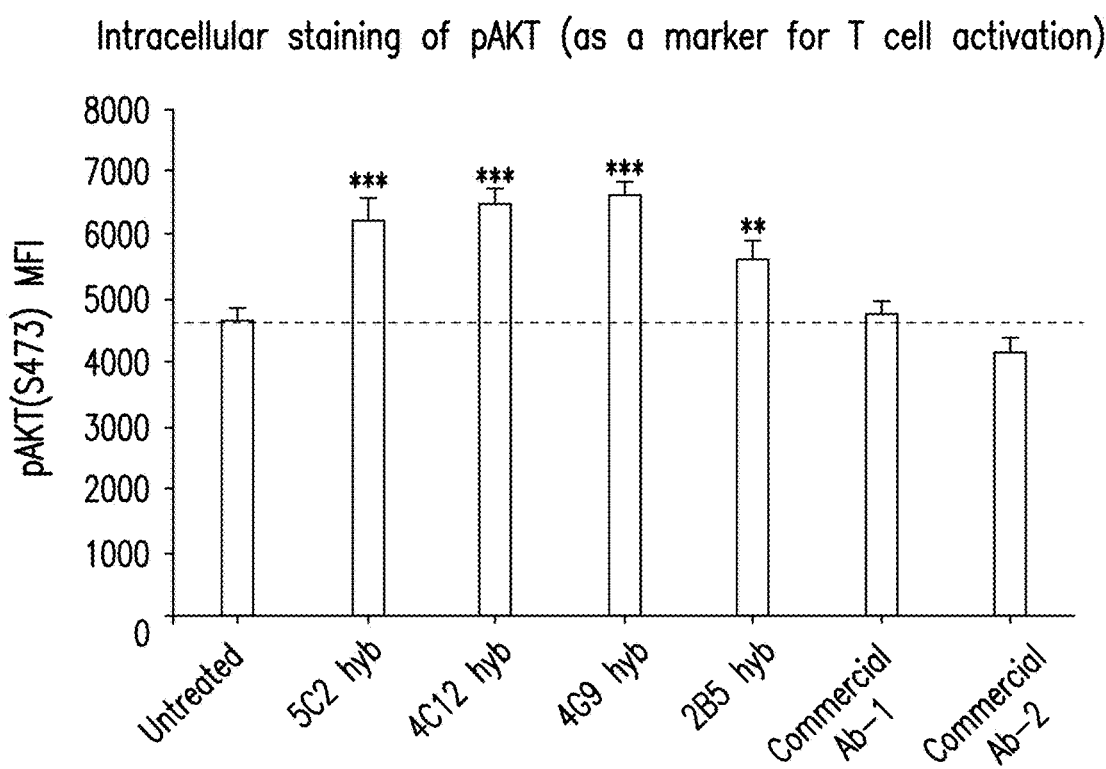
FIG. 8 is a bar graph showing levels of intracellular staining of pAKT in mouse CD4 T cells treated with various antibodies. The X axis represents treatment group and the Y axis represents pAKT (S473) MFI.

Hybridomas from mice immunized with peptide E enhanced the phosphorylation of Akt (S473) in mouse CD4 T cells (FIG. 8).

Example 6: Characterization of Three Anti-PD-1 Antibodies

Materials and Methods

Purified antibodies from hybridomas 5C2, 4C12, and 4G9 were characterized.

Results

Figure 9:
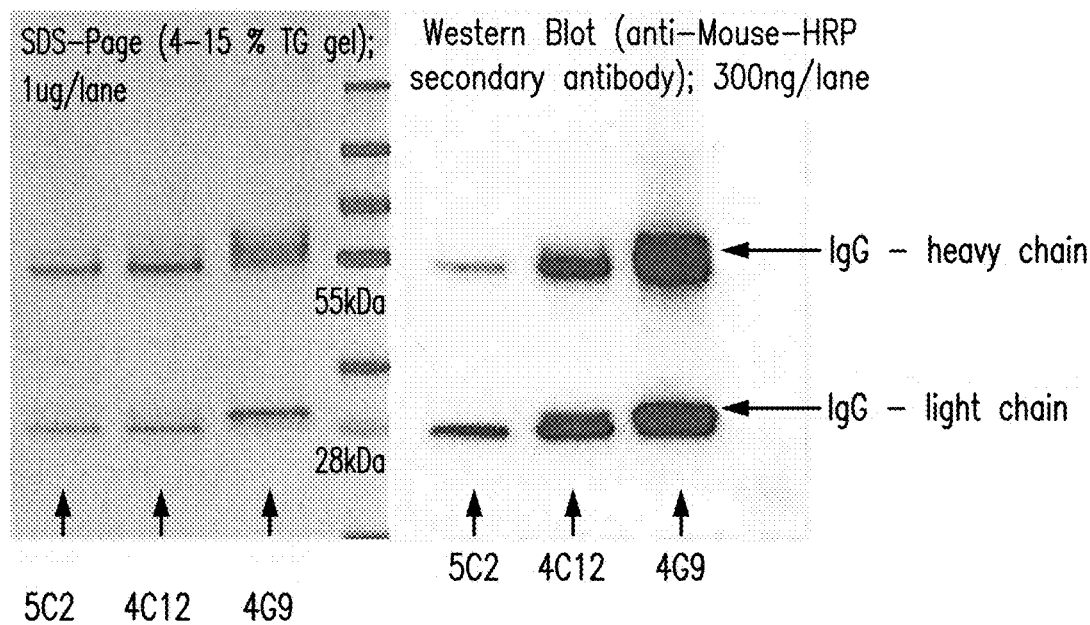
FIG. 9 is a Western blot showing IgG heavy chain and light chain in the various antibodies.

The isotypes for each of the three anti-PD-1 antibodies were determined. 5C2 and 4C12 were both IgG1 isotype and 4G9 was found to be IgG2b isotype (FIG. 9). Hybridoma sequencing showed 100% sequence identity for 5C2 and 4C12 antibodies.

Example 7: 4G9 and 5C2 Specifically Bind to Human PD-1

Materials and Methods:

An ELISA assay was used to determine binding of 4G9 and 5C2 to human PD-1-Fc.

Figure 10:
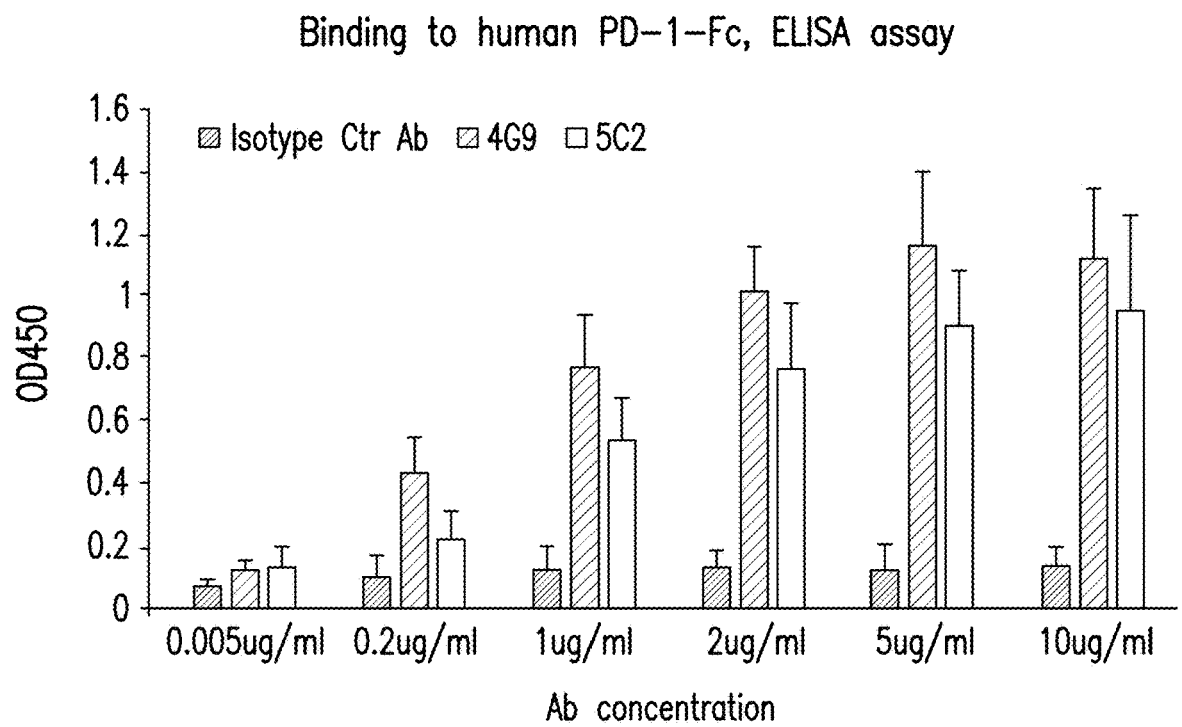
FIG. 10 is a bar graph showing binding of 4G9 and 5C2 antibodies to human PD-1-Fc. The X axis represents antibody concentration and the Y axis represents OD450.
Figure 11A:
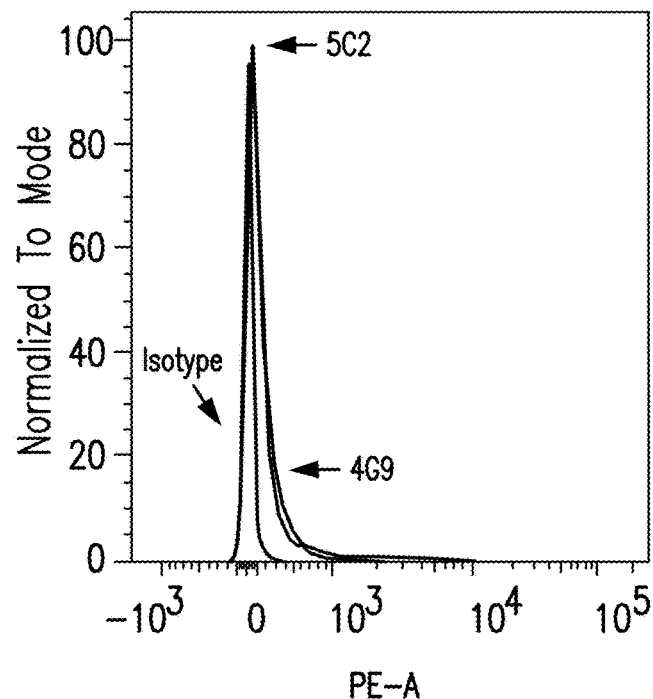
FIGS. 11A and 11B are flow cytometry histograms showing binding of 4G9 and 5C2 antibodies to PD-1 in CD4 T cells from PD-1 KO mice (FIG. 11A) or PD-1 WT mice (FIG. 11B).
Figure 11B:
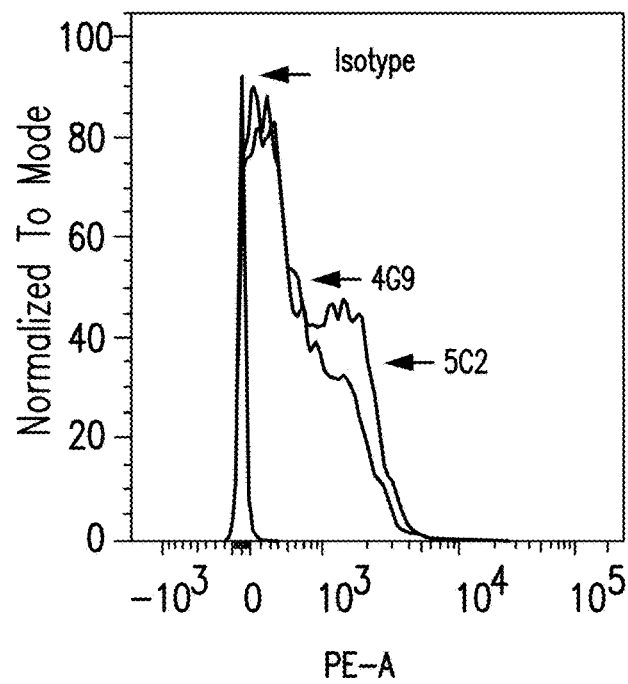
Figure 12:
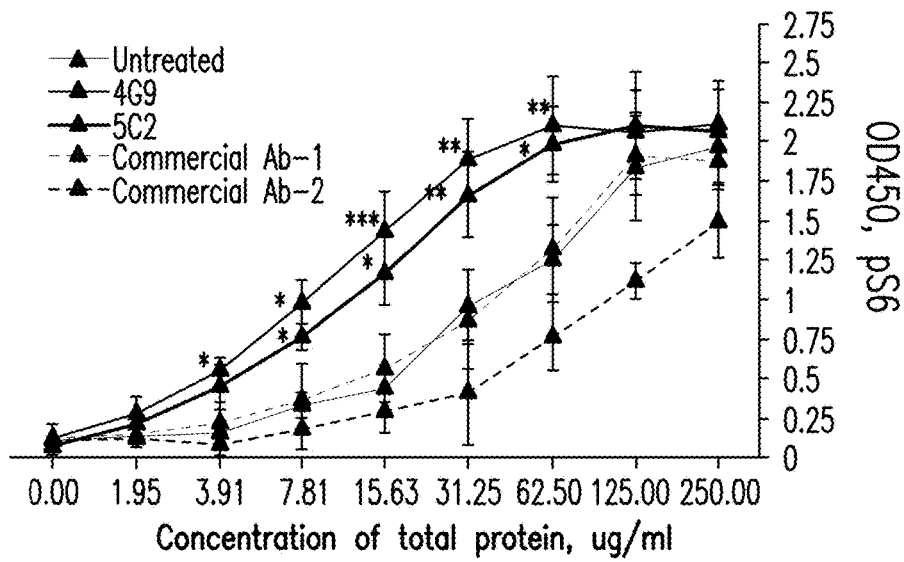
FIG. 12 is a line graph showing pS6 expression in CD4 T cells treated with 4G9 (-▲-), 5C2 (-▲-), commercial Ab-1 (-▲-), commercial Ab-2 (-▲-), or untreated (-▲-). The X axis represents concentration of total protein (μg/ml) and the Y axis represents OD450.

Results:

FIG. 10 shows the results of an ELISA assay to evaluate binding of 4G9 and 5C2 antibodies to human PD-1-Fc. 4G9 and 5C2 both specifically bind to human PD-1. FIG. 11A is a flow cytometry histogram showing that 4G9 and 5C2 do not bind PD-1 KO CD4 T cells, while they do bind CD4 T cells from wild-type mice (FIG. 11B).

Example 8: Signaling

Materials and Methods:

Mouse CD4 T cells were pre-stimulated for 48 hours to ensure PD-1 expression then treated with purified 4G9 and 5C2 antibodies. The concentration of pS6 was determined using an ELISA kit (Cell Signaling Tech).

Results:

In contrast to blocking antibodies (RMP1-14 and J43), 4G9 and 5C2 activate T cells through S6 pathway. Treatment of 48h pre-stimulated (to ensure PD-1 expression) mouse CD4 T cells with purified 4G9 and 5C2 antibodies led to significant increase of pS6 within the linear range (ELISA kit Cell Signaling Tech, *P<0.05, P<0.01, *P<0.001 compared to Untreated). This phenomenon is due to a direct activation rather than PD-1/PD-L1 blockade since treatment with Commercial Ab-1 (RMP1-14) and Ab-2 (J43) that blocks PD-1/PD-L1 interaction does not result in pS6 increase.

Example 8: In Vivo Efficacy Evaluation

Figure 13A:
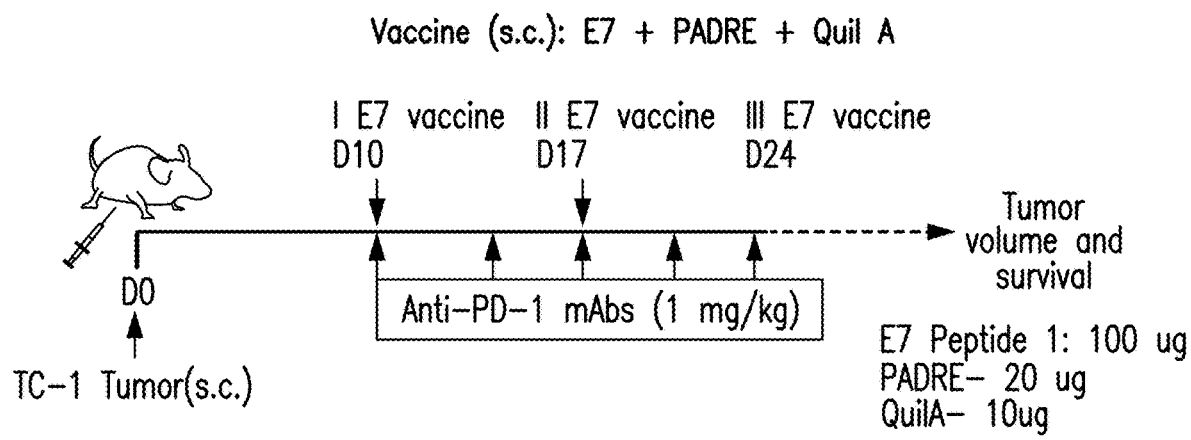
FIG. 13A is a schematic illustration showing the experimental design for the TC-1 tumor experiments.

Materials and Methods:

FIG. 13A is a schematic illustration of the TC-1 tumor model used in this experiment. Briefly, mice were subcutaneously injected with TC-1 tumor cells at day 0. At day 10 (D10), day 17 (D17), and day 24 (D24) after tumor injection, mice were treated with vaccine (E7+PADRE+Quil A). Mice were treated with anti-PD-1 antibodies at day 10, day 14, day 17, day 21, day 24, and day 28.

Figure 13B:
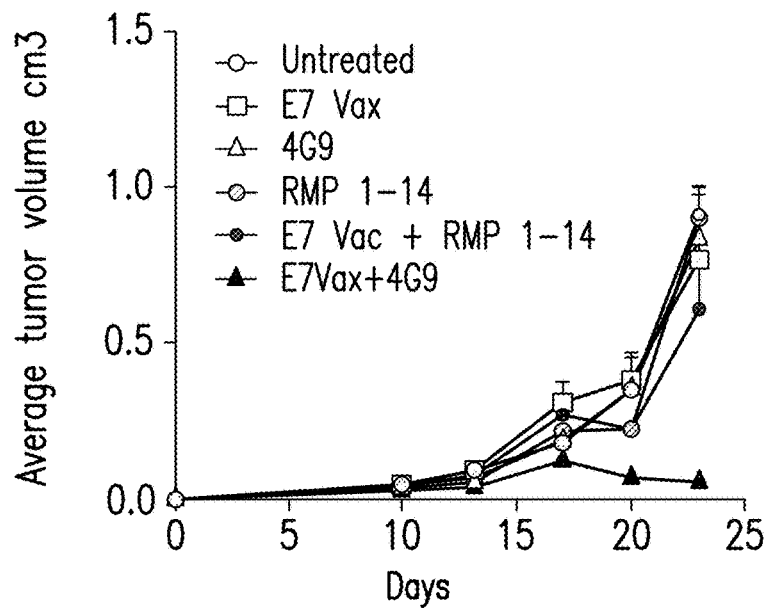
FIG. 13B is a line graph showing average tumor volume ($cm^3$) over time (days) for TC-1 tumor bearing mice treated with E7 Vax (□), 4G9 (△), RMP 1-14 (-✧-) E7 Vax+RMP 1-14 (●), E7 Vax+4G9 (▲), or untreated (○). The X axis represents time (days) and the Y axis represents average tumor volume ($cm^3$).
Figure 13C:
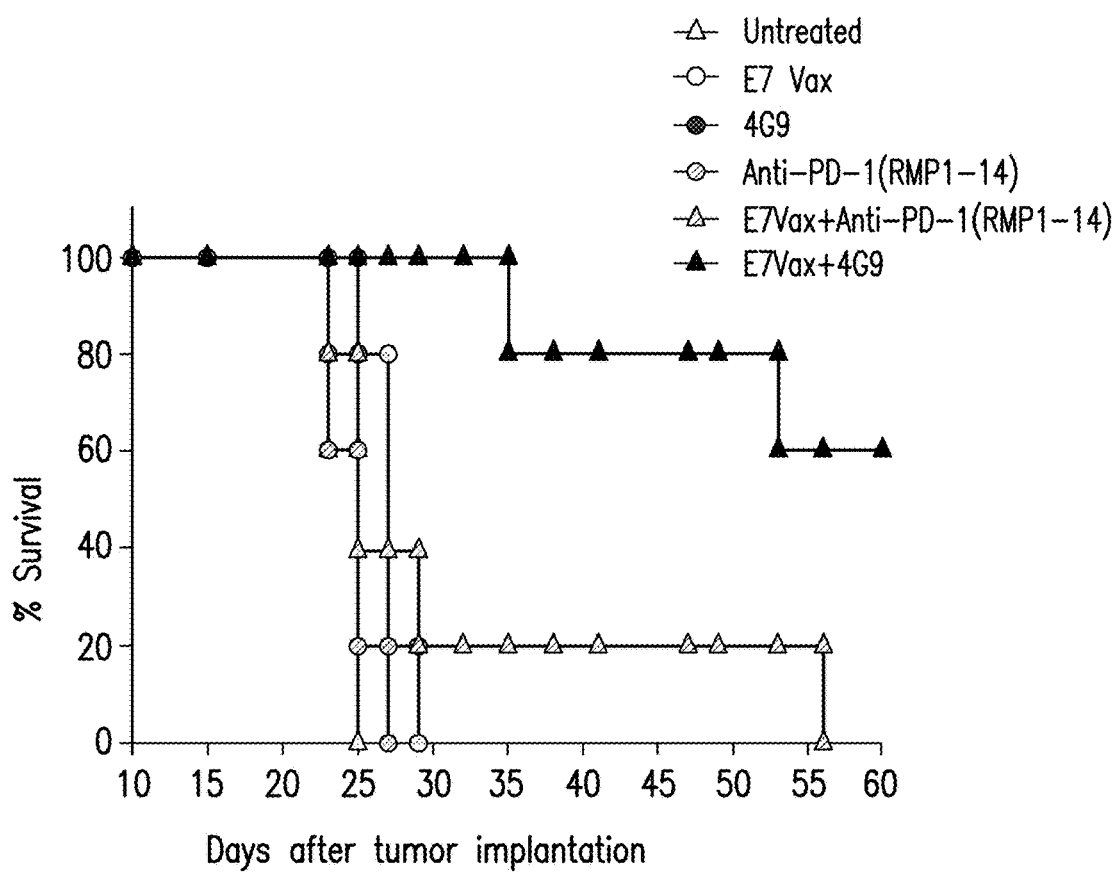
FIG. 13C is a line graph showing percent survival over time for TC-1 tumor bearing mice treated with E7 Vax (○), 4G9 (●), RMP 1-14 (◐), E7 Vax+RMP 1-14 (-✦-), E7 Vax+4G9 (▲), or untreated (△).
Figure 13D:
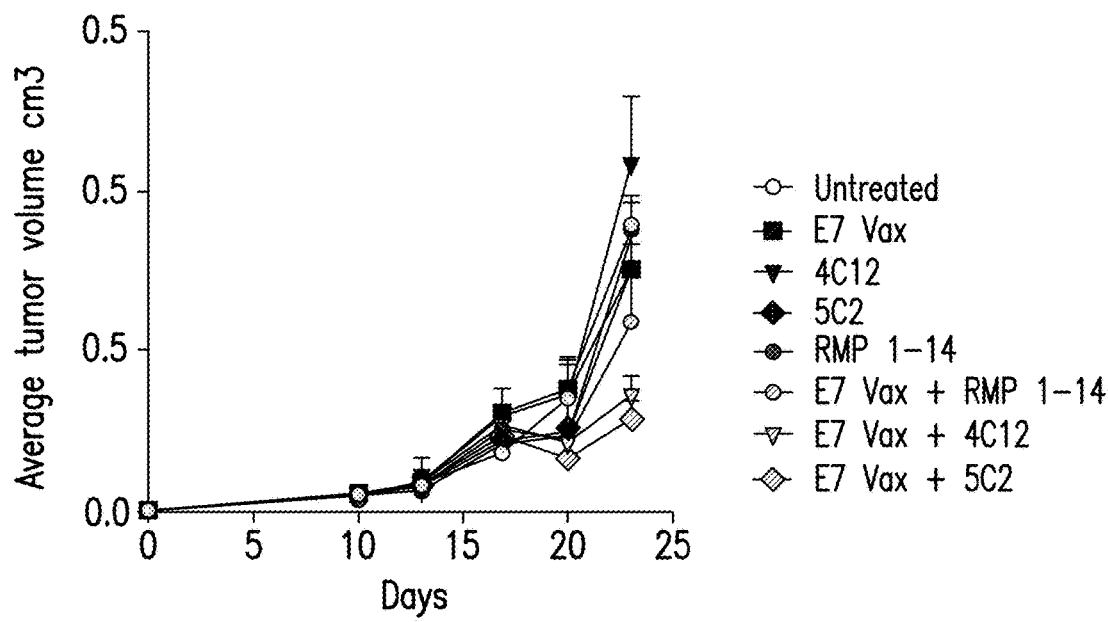
FIG. 13D is a line graph showing average tumor volume ($cm^3$) over time (days) for TC-1 tumor bearing mice treated with E7 Vax (■), 4C12 (▼), 5C2 (♦), RMP 1-14 (●), E7 Vax+RMP 1-14 (-✧-), E7 Vax+4C12 (-✧-), E7 Vax+5C2 (-✧-), or untreated (○).

Results:

Anti-PD-1 antibodies 4G9, 4C12, and 5C2 reduced tumor volume and increased survival when combined with E7 vaccine (FIG. 13B-13D).

Example 9: In Vivo Efficacy Evaluation—Anti-EpE Antibodies

Figure 14A:
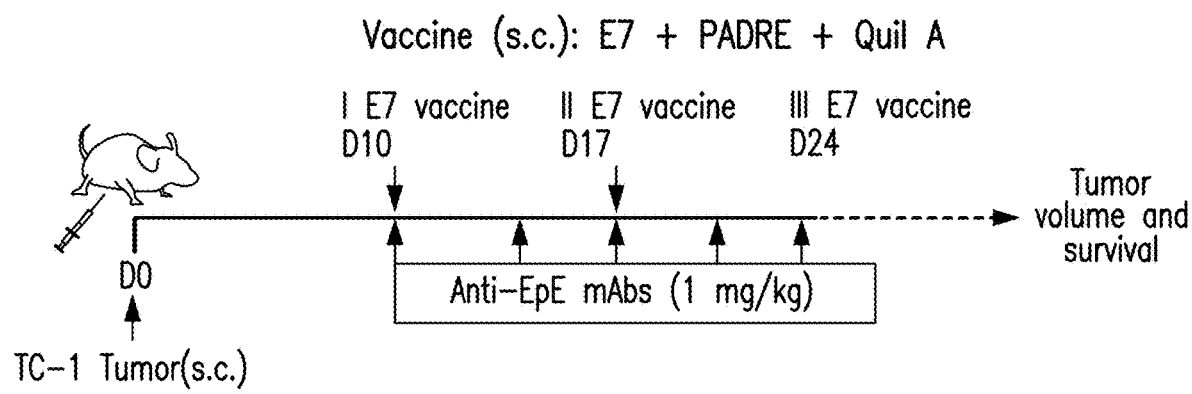
FIG. 14A is a schematic illustration of the experimental design for the TC-1 tumor experiments.

Materials and Methods:

Antibodies against epitope E were generated and tested in the TC-1 tumor model as described in Example 8 above and FIG. 14A.

Figure 14B:
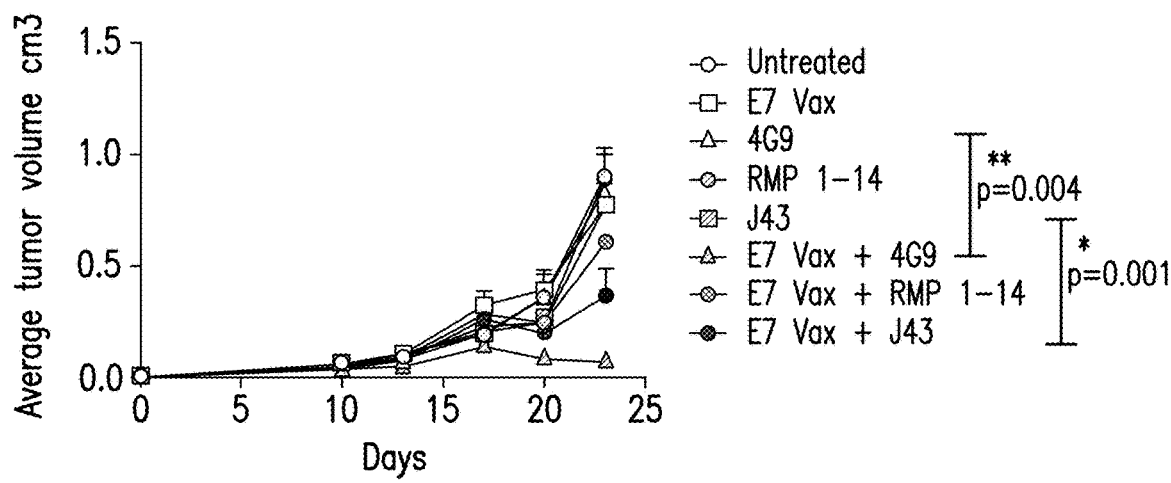
FIG. 14B is a line graph showing average tumor volume ($cm^3$) over time (days) for TC-1 tumor bearing mice treated with E7 Vax (□), 4G9 (△), RMP 1-14 (-✧-), J43 (-✧-), E7 Vax+4G9 (-✧-), E7 Vax+RMP 1-14 (-✧-), E7 Vax+J43 (●), or untreated (○), The X axis represents time (days) and the Y axis represents average tumor volume ($cm^3$).
Figure 14C:
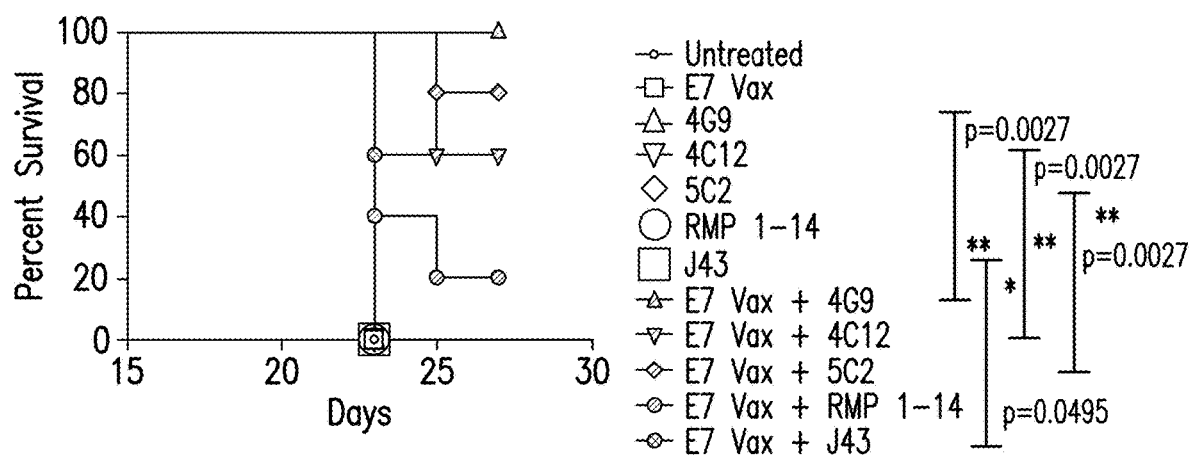
FIG. 14C is a line graph showing percent survival over time of TC-1 tumor bearing mice treated with E7 Vax (□), 4G9 (△), 4C12 (▼), 5C2 (◇), RMP 1-14 (○), J43 (□), E7 Vax+4G9 (-✧-), E7 Vax+4C12 (-✧-), E7 Vax+5C2 (-✧-) E7 Vax+RMP 1-14 (-✧-), E7 Vax+J43 (-✧-), or untreated (-✧-). The X axis represents time (days) and the Y axis represents percent survival.

Results:

Mice treated with 4G9, an antibody generated against epitope E, exhibited significantly lower tumor volume and higher survival rate when compared to traditional checkpoint inhibitors, anti-PD1 blocking antibodies RMP1-14 and J43 (FIG. 14B-14C).

We claim:

1. A nucleic acid that encodes for an antibody or an antigen-binding fragment thereof that immunospecifically binds to PD-1, wherein the antibody or the antigen-binding fragment thereof comprises three heavy chain CDRs (HCDR1, HCDR2, and HCDR3) contained within the heavy chain variable region (HCVR) sequence of SEQ ID NO:27 or 28; and three light chain CDRs (LCDR1, LCDR2, LCDR3) contained within the light chain variable region (LCVR) sequence of SEQ ID NO:33 or 34.

2. The nucleic acid of claim 1, wherein the HCDR1 domain has an amino acid sequence of SEQ ID NO:29; the HCDR2 domain has an amino acid sequence of SEQ ID NO:30; the HCDR3 domain has an amino acid sequence of SEQ ID NO:31; the LCDR1 domain has an amino acid sequence of SEQ ID NO:35; the LCDR2 domain has an amino acid sequence of SEQ ID NO:36; and the LCDR3 domain has an amino acid sequence of SEQ ID NO: 37.

3. The nucleic acid of claim 1, wherein the antibody or the antigen-binding fragment thereof comprises an amino acid sequence of the heavy chain variable region of SEQ ID NO:27 or 28, or an amino acid sequence with at least 80% sequence identity thereto.

4. The nucleic acid of claim 1, wherein the antibody or the antigen-binding fragment thereof comprises an amino acid sequence of the light chain variable region of SEQ ID NO:33 or 34, or an amino acid sequence with at least 80% sequence identity thereto.

5. The nucleic acid of claim 1, wherein the antibody or the antigen-binding fragment thereof comprises an amino acid sequence of the heavy chain variable region of SEQ ID NO:27 or 28, or an amino acid sequence with at least 80% sequence identity thereto; and an amino acid sequence of the light chain variable region of SEQ ID NO:33 or 34, or an amino acid sequence with at least 80% sequence identity thereto.

6. The nucleic acid of claim 1, wherein the antibody or the antigen-binding fragment thereof comprises a heavy chain that has an amino acid sequence of SEQ ID NO:27 or 28, or an amino acid sequence with at least 80% sequence identity thereto.

7. The nucleic acid of claim 1, wherein the antibody or the antigen-binding fragment thereof comprises a light chain that has an amino acid sequence of SEQ ID NO:33 or 34, or an amino acid sequence with at least 80% sequence identity thereto.

8. The nucleic acid of claim 1, wherein the antibody or the antigen-binding fragment thereof comprises a heavy chain that has an amino acid sequence of SEQ ID NO:27 or 28, or an amino acid sequence with at least 80% sequence identity thereto; and a light chain that has an amino acid sequence of SEQ ID NO:33 or 34, or an amino acid sequence with at least 80% sequence identity thereto.

9. The nucleic acid of claim 1, wherein the antibody or the antigen-binding fragment thereof comprises a heavy chain constant region.

10. The nucleic acid of claim 9, wherein the heavy chain constant region is an IgG constant region.

11. The nucleic acid of claim 1, wherein the antibody or the antigen-binding fragment thereof comprises a light chain constant region.

12. The nucleic acid of claim 1, wherein the antibody or the antigen-binding fragment thereof comprises a heavy chain constant region and a light chain constant region.

13. The nucleic acid of claim 1, wherein the antibody or the antigen-binding fragment thereof is an immunoglobulin type selected from the group consisting of IgG, IgE, IgM, IgD, IgA, and IgY.

14. The nucleic acid of claim 1, wherein the antibody or the antigen-binding fragment thereof is an immunoglobulin class selected from the group consisting of IgG1, IgG2, IgG3, IgG4, IgA1, and IgA2.

15. The nucleic acid of claim 1, wherein the antibody or the antigen-binding fragment thereof is an antigen-binding fragment selected from the group consisting of Fab', F (ab')2, Fv, single chain (ScFv), diScFv, diabody, and tribody.

16. The nucleic acid of claim 1, wherein the antibody or the antigen-binding fragment thereof is a whole immunoglobulin.

17. The nucleic acid of claim 1, wherein the antibody or antigen-binding fragment thereof is human, mouse, chimeric, humanized, or monoclonal.

18. The nucleic acid of claim 1, wherein the antibody or antigen-binding fragment thereof is bispecific, trispecific, or multispecific.

19. A cell for producing the antibody or antigen-binding fragment thereof that specifically binds to PD-1, comprising the nucleic acid of claim 1.

20. The cell of claim 19, wherein the nucleic acid is a vector.

21. The cell of claim 20, wherein the vector is an expression vector.

* * * * *

SEQUENCE LISTING

```
Sequence total quantity: 38
SEQ ID NO: 1           moltype = AA  length = 288
FEATURE                Location/Qualifiers
source                 1..288
                       mol_type = protein
                       organism = Homo sapiens
SEQUENCE: 1
MQIPQAPWPV VWAVLQLGWR PGWFLDSPDR PWNPPTFSPA LLVVTEGDNA TFTCSFSNTS   60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
```

```
CVPEQTEYAT IVFPSGMGTS SPARRGSADG PRSAQPLRPE DGHCSWPL              288

SEQ ID NO: 2            moltype = AA   length = 288
FEATURE                 Location/Qualifiers
source                  1..288
                        mol_type = protein
                        organism = Mus musculus
SEQUENCE: 2
MWVRQVPWSF TWAVLQLSWQ SGWLLEVPNG PWRSLTFYPA WLTVSEGANA TFTCSLSNWS   60
EDLMLNWNRL SPSNQTEKQA AFCNGLSQPV QDARFQIIQL PNRHDFHMNI LDTRRNDSGI  120
YLCGAISLHP KAKIEESPGA ELVVTERILE TSTRYPSPSP KPEGRFQGMV IGIMSALVGI  180
PVLLLLAWAL AVFCSTSMSE ARGAGSKDDT LKEEPSAAPV PSVAYEELDF QGREKTPELP  240
TACVHTEYAT IVFTEGLGAS AMGRRGSADG LQGPRPPRHE DGHCSWPL               288

SEQ ID NO: 3            moltype = DNA   length = 1389
FEATURE                 Location/Qualifiers
source                  1..1389
                        mol_type = other DNA
                        organism = synthetic construct
SEQUENCE: 3
atgagatgga gctgtatcat cctcttcttg gtagcaacag ctacaggtgt ccactcccag   60
gtccaactgc agcagcctgg ggctgaactg gtgaagcctg gggcttcagt gaaggtgtcc  120
tgcaaggctt ctggctacac cttcaccagc tactggatgc actgggtgaa gcagaggcct  180
ggccaaggcc ttgagtggat tggaaggatt catccttctg atagtgatac taactacaat  240
caaaagttca agggcaaggc cacattgact gtagacaaat cctccagcac agcctacatg  300
cagctcagca gcctgacatc tgaggactct gcggtctatt actgtgcacc tatggtaac  360
tacgcctccg ggtttgctta ctggggccaa gggactctgg tcactgtctc tgcagccaaa  420
acgacacccc catctgtcta tccactggcc cctggatctg ctgccaaaac taactccatg  480
gtgaccctgg gatgcctggt caagggctat ttccctgagc cagtgacagt gacctggaac  540
tctggatccc tgtccagcgg tgtgcacacc ttcccagctg tcctgcagtc tgacctctac  600
actctgagca gctcagtgac tgtcccctcc agcacctgga ccagccagac cgtcacctgc  660
aacgttgccc accggccag cagcaccaag gtggacaaga aaattgtgcc cagggattgt  720
ggttgtaagc cttgcatatg tacagtccca gaagtatcat ctgtcttcat cttcccccca  780
aagcccaagg atgtgctcac cattactctg actcctccag tcaagtgtgt tgtggtagac  840
atcagcaagg atgatcccga ggtccagttc agctggtttg tagatgatgt ggaggtgcac  900
acagctcaga cgaaaccccg ggaggagcag atcaacagca ctttccgttc agtcagtgaa  960
cttcccatca tgcaccagga ctggctcaat ggcaaggagt tcaaatgcag ggtcaacagt 1020
gcagctttcc ctgcccccat cgagaaaacc atctccaaaa ccaaaggcag accgaaggct 1080
ccacaggtgt acaccattcc acctcccaag gagcagatgg ccaaggataa attcagtctg 1140
acctgcatga taacaaactt cttccctgaa gacattactg tggagtggca gtggaatggg 1200
cagccagcgg agaactacaa gaacactcag cccatcatgg acacagatgg ctcttacttc 1260
gtctacagca agctcaatgt gcagaagagc aactgggagg caggaaatac tttcacctgc 1320
tctgtgttac atgagggcct gcacaaccac catactgaga gagcctctc ccactctcct 1380
ggtaaatga                                                          1389

SEQ ID NO: 4            moltype = AA   length = 462
FEATURE                 Location/Qualifiers
source                  1..462
                        mol_type = protein
                        organism = synthetic construct
SEQUENCE: 4
MRWSCIILFL VATATGVHSQ VQLQQPGAEL VKPGASVKVS CKASGYTFTS YWMHWVKQRP   60
GQGLEWIGRI HPSDSDTNYN QKFKGKATLT VDKSSSTAYM QLSSLTSEDS AVYYCAPYGN  120
YASGFAYWGQ GTLVTVSAAK TTPPSVYPLA PGSAAQTNSM VTLGCLVKGY FPEPVTVTWN  180
SGSLSSGVHT FPAVLQSDLY TLSSSVTVPS STWPSQTVTC NVAHPASSTK VDKKIVPRDC  240
GCKPCICTVP EVSSVFIFPP KPKDVLTITL TPKVTCVVVD ISKDDPEVQF SWFVDDVEVH  300
TAQTKPREEQ INSTFRSVSE LPIMHQDWLN GKEFKCRVNS AAFPAPIEKT ISKTKGRPKA  360
PQVYTIPPPK EQMAKDKVSL TCMITNFFPE DITVEWQWNG QPAENYKNTQ PIMDTDGSYF  420
VYSKLNVQKS NWEAGNTFTC SVLHEGLHNH HTEKSLSHSP GK                     462

SEQ ID NO: 5            moltype = AA   length = 443
FEATURE                 Location/Qualifiers
source                  1..443
                        mol_type = protein
                        organism = synthetic construct
SEQUENCE: 5
QVQLQQPGAE LVKPGASVKV SCKASGYTFT SYWMHWVKQR PGQGLEWIGR IHPSDSDTNY   60
NQKFKGKATL TVDKSSSTAY MQLSSLTSED SAVYYCAPYG NYASGFAYWG QGTLVTVSAA  120
KTTPPSVYPL APGSAAQTNS MVTLGCLVKG YFPEPVTVTW NSGSLSSGVH TFPAVLQSDL  180
YTLSSSVTVP SSTWPSQTVT CNVAHPASST KVDKKIVPRD CGCKPCICTV PEVSSVFIFP  240
PKPKDVLTIT LTPKVTCVVV DISKDDPEVQ FSWFVDDVEV HTAQTKPREE QINSTFRSVS  300
ELPIMHQDWL NGKEFKCRVN SAAFPAPIEK TISKTKGRPK APQVYTIPPP KEQMAKDKVS  360
LTCMITNFFP EDITVEWQWN GQPAENYKNT QPIMDTDGSY FVYSKLNVQK SNWEAGNTFT  420
CSVLHEGLHN HHTEKSLSHS PGK                                          443

SEQ ID NO: 6            moltype = AA   length = 5
FEATURE                 Location/Qualifiers
source                  1..5
                        mol_type = protein
```

```
                                    -continued organism = synthetic construct
SEQUENCE: 6
SYWMH                                                                        5

SEQ ID NO: 7              moltype = AA   length = 17
FEATURE                   Location/Qualifiers
source                    1..17
                          mol_type = protein
                          organism = synthetic construct
SEQUENCE: 7
RIHPSDSDTN YNQKFKG                                                          17

SEQ ID NO: 8              moltype = AA   length = 10
FEATURE                   Location/Qualifiers
source                    1..10
                          mol_type = protein
                          organism = synthetic construct
SEQUENCE: 8
YGNYASGFAY                                                                  10

SEQ ID NO: 9              moltype = DNA  length = 717
FEATURE                   Location/Qualifiers
source                    1..717
                          mol_type = other DNA
                          organism = synthetic construct
SEQUENCE: 9
atgggcatca agatggagtc acagattcag gcatttgtat tcgtgtttct ctggttgtct           60
ggtgttgacg gagacattgt gatgacccag tctcacaaat tcatgtccac atcagtagga         120
gacagggtca gcatcacctg caaggccagt caggatgtga gtactgctgt agcctggtat         180
caacaaaaac cagggcaatc tcctaaaacta ctgatttact gggcatccac ccggcacact        240
ggagtccctg atcgcttcac aggcagtgga tctgggacag attatactct caccatcagc         300
agtgtgcagg ctgaagacct ggcactttat tactgtcagc aacattatag cactccgtgg         360
acgttcggtg aggcaccaa gctggaaatc aaacgggctg atgctgcacc aactgtatcc          420
atcttcccac catccagtga gcagttaaca tctggaggtg cctcagtcgt gtgcttcttg         480
aacaacttct acccaaaga catcaatgtc aagtggaaa ttgatggcag tgaacgacaa           540
aatggcgtcc tgaacagttg gactgatcag gacagcaaag acagcaccta cagcatgagc         600
agcaccctca cgttgaccaa ggacgagtat aacgacata acagctatac ctgtgaggcc          660
actcacaaga catcaacttc acccattgtc aagagcttca caggaatga gtgttag             717

SEQ ID NO: 10             moltype = AA   length = 238
FEATURE                   Location/Qualifiers
source                    1..238
                          mol_type = protein
                          organism = synthetic construct
SEQUENCE: 10
MGIKMESQIQ AFVFVFLWLS GVDGDIVMTQ SHKFMSTSVG DRVSITCKAS QDVSTAVAWY           60
QQKPGQSPKL LIYWASTRHT GVPDRFTGSG SGTDYTLTIS SVQAEDLALY YCQQHYSTPW         120
TFGGGTKLEI KRADAAPTVS IFPPSSEQLT SGGASVVCFL NNFYPKDINV KWKIDGSERQ         180
NGVLNSWTDQ DSKDSTYSMS STLTLTKDEY ERHNSYTCEA THKTSTSPIV KSFNRNEC           238

SEQ ID NO: 11             moltype = AA   length = 214
FEATURE                   Location/Qualifiers
source                    1..214
                          mol_type = protein
                          organism = synthetic construct
SEQUENCE: 11
DIVMTQSHKF MSTSVGDRVS ITCKASQDVS TAVAWYQQKP GQSPKLLIYW ASTRHTGVPD           60
RFTGSGSGTD YTLTISSVQA EDLALYYCQQ HYSTPWTFGG GTKLEIKRAD AAPTVSIFPP         120
SSEQLTSGGA SVVCFLNNFY PKDINVKWKI DGSERQNGVL NSWTDQDSKD STYSMSSTLT         180
LTKDEYERHN SYTCEATHKT STSPIVKSFN RNEC                                     214

SEQ ID NO: 12             moltype = AA   length = 11
FEATURE                   Location/Qualifiers
source                    1..11
                          mol_type = protein
                          organism = synthetic construct
SEQUENCE: 12
KASQDVSTAV A                                                                11

SEQ ID NO: 13             moltype = AA   length = 7
FEATURE                   Location/Qualifiers
source                    1..7
                          mol_type = protein
                          organism = synthetic construct
SEQUENCE: 13
WASTRHT                                                                      7

SEQ ID NO: 14             moltype = AA   length = 9
FEATURE                   Location/Qualifiers
```

```
source                   1..9
                         mol_type = protein
                         organism = synthetic construct
SEQUENCE: 14
QQHYSTPWT                                                                  9

SEQ ID NO: 15            moltype = DNA   length = 1773
FEATURE                  Location/Qualifiers
source                   1..1773
                         mol_type = other DNA
                         organism = synthetic construct
SEQUENCE: 15
atggaatgga gcagagtctt tatctttctc ctatcagtaa ctgcaggtgt tcactcccag         60
gtccagctgc agcagtctgg agctgagctg gtaaggcctg ggacttcagt gaaggtgtcc        120
tgcaaggctt ctggatacgc cttcactaat tacttgatag agtgggtaaa gcagaggcct        180
ggacagggcc ttgagtggat tggagtgatt aatcctggaa gtggtggtac taactacaat        240
gagaagttca agggcaaggc aacactgact gcagacaaat cctccagcac tgcctacatg        300
cagctcagca gcctgacatc tgaggactct gcggtctatt tctgtgcaag atcagctgca        360
gcccctgact actggggcca aggcaccact ctcacagtct cctcagagag tcagtccttc        420
ccaaatgtct tccccctcgt ctcctgcgag agccccctgt ctgataagaa tctggtggcc        480
atgggctgcc tggcccggga cttcctgccc agcaccattt ccttcacctg gaactaccag        540
aacaacactg aagtcatcca gggtatcaga accttccaga gggggcaagg        600
tacctagcca cctcgcaggt gttgctgtct cccaagagca tccttgaagg ttcagatgaa        660
tacctggtat gcaaaatcca ctacggaggc aaaaacaaag atctgcatgt gcccattcca        720
gctgtcgcag agatgaaccc caatgtaaat gtgttcgtcc caccacggga tggcttctct        780
ggccctgcac cagcaagtc taaactcatc tgcgaggcca cgaacttcac tccaaaaccg        840
atcacagtat cctggctaaa ggatgggaag ctcgtggaat ctggcttcac cacagatccg        900
gtgaccatcg agaacaaagg atccacaccc caaacctaca aggtcataag cacacttacc        960
atctctgaaa tcgactggct gaacctgaat gtgtacacct gccgtgtgga tcacagggg        1020
ctcacctttc tgaagaacgt gtcctccaca tgtgctgcca gtccctgcca agatcatccta      1080
accttcacca tccccccctc ctttgccgac atcttcctca gcaagtccgc taacctgacc       1140
tgtctggtct caaacctggc aacctatgaa accctgaata tctcctgggc ttctcaaagt       1200
ggtgaaccac tggaaccaa aattaaaatc atggaaagcc atcccaatgg caccttcagt        1260
gctaagggtg tggctagtgt ttgtgtggaa gactggaata acaggaagga atttgtgtgt       1320
actgtgactc acagggatct gccttcacca cagaagaaat tcatctcaaa acccaatgag       1380
gtgcacaaac atccacctgc tgtgtacctg ctgccaccag ctcgtgagca actgaacctg       1440
agggagtcag ccacagtcac ctgcctggtg aagggcttct ctcctgcaga catcagtgtg       1500
cagtggcttc agaggggca actcttgccc aagagaagt atgtgaccag tgccccgatg         1560
ccagagcctg ggccccagg cttctacttt acccacagca tcctgactgt gacagaggag       1620
gaatggaact ccggagagac ctatacctgt gttgtaggcc acgaggccct gccacacctg       1680
gtgaccgaga ggaccgtgga caagtccact ggtaaaccca cactgtacaa tgtctccctg       1740
atcatgtctg acacaggcgg cacctgctat tga                                    1773

SEQ ID NO: 16            moltype = AA   length = 590
FEATURE                  Location/Qualifiers
source                   1..590
                         mol_type = protein
                         organism = synthetic construct
SEQUENCE: 16
MEWSRVFIFL LSVTAGVHSQ VQLQQSGAEL VRPGTSVKVS CKASGYAFTN YLIEWVKQRP         60
GQGLEWIGVI NPGSGGTNYN EKFKGKATLT ADKSSSTAYM QLSSLTSEDS AVYFCARSAQ        120
APDYWGQGTT LTVSSESQSF PNVFPLVSCE SPLSDKNLVA MGCLARDFLP STISFTWNYQ        180
NNTEVIQGIR TFPTLRTGGK YLATSQVLLS PKSILEGSDE YLVCKIHYGG KNKDLHVPIP        240
AVAEMNPNVN VFVPPRDGFS GPAPRKSKLI CEATNFTPKP ITVSWLKDGK LVESGFTTDP        300
VTIENKGSTP QTYKVISTLT ISEIDWLNLN VYTCRVDHRG LTFLKNVSST CAASPSTDIL        360
TFTIPPSFAD IFLSKSANLT CLVSNLATYE TLNISWASQS GEPLETKIKI MESHPNGTFS        420
AKGVASVCVE DWNNRKEFVC TVTHRDLPSP QKKFISKPNE VHKHPPAVYL LPPAREQLNL        480
RESATVTCLV KGFSPADISV QWLQRGQLLP QEKYVTSAPM PEPGAPGFYF THSILTVTEE        540
EWNSGETYTC VVGHEALPHL VTERTVDKST GKPTLYNVSL IMSDTGGTCY                   590

SEQ ID NO: 17            moltype = AA   length = 571
FEATURE                  Location/Qualifiers
source                   1..571
                         mol_type = protein
                         organism = synthetic construct
SEQUENCE: 17
QVQLQQSGAE LVRPGTSVKV SCKASGYAFT NYLIEWVKQR PGQGLEWIGV INPGSGGTNY         60
NEKFKGKATL TADKSSSTAY MQLSSLTSED SAVYFCARSA QAPDYWGQGT TLTVSSESQS        120
FPNVFPLVSC ESPLSDKNLV AMGCLARDFL PSTISFTWNY QNNTEVIQGI RTFPTLRTGG        180
KYLATSQVLL SPKSILEGSD EYLVCKIHYG GKNKDLHVPI PAVAEMNPNV NVFVPPRDGF        240
SGPAPRKSKL ICEATNFTPK PITVSWLKDG KLVESGFTTD PVTIENKGST PQTYKVISTL        300
TISEIDWLNL NVYTCRVDHR GLTFLKNVSS TCAASPSTDI LTFTIPPSFA DIFLSKSANL        360
TCLVSNLATY ETLNISWASQ SGEPLETKIK IMESHPNGTF SAKGVASVCV EDWNNRKEFV        420
CTVTHRDLPS PQKKFISKPN EVHKHPPAVY LLPPAREQLN LRESATVTCL VKGFSPADIS        480
VQWLQRGQLL PQEKYVTSAP MPEPGAPGFY FTHSILTVTE EEWNSGETYT CVVGHEALPH        540
LVTERTVDKS TGKPTLYNVS LIMSDTGGTC Y                                       571

SEQ ID NO: 18            moltype = AA   length = 5
FEATURE                  Location/Qualifiers
```

```
source                       1..5
                             mol_type = protein
                             organism = synthetic construct
SEQUENCE: 18
NYLIE                                                                    5

SEQ ID NO: 19                moltype = AA   length = 17
FEATURE                      Location/Qualifiers
source                       1..17
                             mol_type = protein
                             organism = synthetic construct
SEQUENCE: 19
VINPGSGGTN YNEKFKG                                                      17

SEQ ID NO: 20                moltype = AA   length = 7
FEATURE                      Location/Qualifiers
source                       1..7
                             mol_type = protein
                             organism = synthetic construct
SEQUENCE: 20
SAQAPDY                                                                  7

SEQ ID NO: 21                moltype = DNA   length = 717
FEATURE                      Location/Qualifiers
source                       1..717
                             mol_type = other DNA
                             organism = synthetic construct
SEQUENCE: 21
atgggcatca agatggagac acattctcag gtctttgtat acatgttgct gtggttgtct       60
ggtgttgaag gagacattgt gatgacccag tctcacaaat tcatgtccac atcagtagga      120
gacagggtca gcatcacctg caaggccagt caggatgtgg gtactgctgt agcctgtat       180
caacagaaac cagggcaatc tcctaaacta ctgatttact gggcatccac ccggcacact      240
ggagtccctg atcgcttcac aggcagtgga tctgggacag atttcactct caccattagc      300
aatgtgcagt ctgaagactt ggcagattat ttctgtcagc aatatagcac ctatccattc      360
acgttcggct cggggacaaa gttggaaata aaacgggctg atgctgcacc aactgtatcc      420
atcttcccac catccagtga gcagttaaca tctggaggtg cctcagtcgt gtgcttcttg      480
aacaacttct accccaaaga catcaatgtc aagtggaaga ttgatggcag tgaacgacaa      540
aatggcgtcc tgaacagttg gactgatcag gacagcaaag acagcaccta cagcatgagc      600
agcaccctca cgttgaccaa ggacgagtat gaacgacata cagctatac ctgtgaggcc      660
actcacaaga catcaacttc acccattgtc aagagcttca caggaatga gtgttag         717

SEQ ID NO: 22                moltype = AA   length = 238
FEATURE                      Location/Qualifiers
source                       1..238
                             mol_type = protein
                             organism = synthetic construct
SEQUENCE: 22
MGIKMETHSQ VFVYMLLWLS GVEGDIVMTQ SHKFMSTSVG DRVSITCKAS QDVGTAVAWY       60
QQKPGQSPKL LIYWASTRHT GVPDRFTGSG SGTDFTLTIS NVQSEDLADY FCQQYSSYPF      120
TFGSGTKLEI KRADAAPTVS IFPPSSEQLT SGGASVVCFL NNFYPKDINV KWKIDGSERQ      180
NGVLNSWTDQ DSKDSTYSMS STLTLTKDEY ERHNSYTCEA THKTSTSPIV KSFNRNEC        238

SEQ ID NO: 23                moltype = AA   length = 214
FEATURE                      Location/Qualifiers
source                       1..214
                             mol_type = protein
                             organism = synthetic construct
SEQUENCE: 23
DIVMTQSHKF MSTSVGDRVS ITCKASQDVS TAVAWYQQKP GQSPKLLIYW ASTRHTGVPD       60
RFTGSGSGTD YTLTISSVQA EDLALYYCQQ HYSTPWTFGG GTKLEIKRAD AAPTVSIFPP      120
SSEQLTSGGA SVVCFLNNFY PKDINVKWKI DGSERQNGVL NSWTDQDSKD STYSMSSTLT      180
LTKDEYERHN SYTCEATHKT STSPIVKSFN RNEC                                  214

SEQ ID NO: 24                moltype = AA   length = 11
FEATURE                      Location/Qualifiers
source                       1..11
                             mol_type = protein
                             organism = synthetic construct
SEQUENCE: 24
KASQDVSTAV A                                                            11

SEQ ID NO: 25                moltype = AA   length = 9
FEATURE                      Location/Qualifiers
source                       1..9
                             mol_type = protein
                             organism = synthetic construct
SEQUENCE: 25
QQHYSTPWT                                                                9
```

| | | | |
|---|---|---|---|
| SEQ ID NO: 26 | moltype = DNA length = 1416 | | |
| FEATURE | Location/Qualifiers | | |
| source | 1..1416 | | |
| | mol_type = other DNA | | |
| | organism = synthetic construct | | |

SEQUENCE: 26

```
atgggttggc tgtgtgaactt gctattcctg atggcagctg cccaaagtgc ccaagcacag   60
atccagttgg tacagtctgg acctgagctg aagaagcctg gagagacagt caagatctcc  120
tgcaaggctt ctgggtatac cttcacaacc tatggaatga cctgggtgaa acaggctcca  180
ggaaagggtt taaagtggat gggctggata aacacctact ctgggtgtgcc aacatatgct  240
gatgacttca agggacggtt tgccttctct ttggaaacct ctgccagcac tgcctatttg  300
cagatcaaca acctcaaaaa tgaggacacg gctacatatt tctgtgcaag aggggggacgg  360
gggtttgctt actggggcca aggaactctg gtcactgtct ctgcagccaa aacaacaccc  420
ccatcagtct atcccactgg ccctgggtgt ggagatacaa ctggttcctc tgtgactctg  480
ggatgcctgg tcaagggcta cttccctgag tcagtgactg tgacttggaa ctctggatcc  540
ctgtccagca gtgtgcacac cttccctgct ctcctgcagt ctggactcta cactatgagc  600
agctcagtga ctgtcccctc cagcacctgg ccaagtcaga ccgtcacctg cagcgttgct  660
cacccagcca gcaccaccgt tgacaaaaact tcagcccagc ggggcc catttcaacc  720
atcaacccct gtcctccatg caaggagtgt cacaaatgcc cagctcctaa cctcgagggt  780
ggaccatccg tcttcatctt ccctccaaat atcaaggatg tactcatgat ctccctgaca  840
cccaaggtca cgtgtgtggt ggtggatgtg agcgaggatg acccagacgt ccggatcagc  900
tggtttgtga acaacgtgga gtacacacag ctcagacac aaacccatag agaggattac  960
aacagtacta tccgggtggt cagtgccctc cccatccagc accaggactg gatgagtggc 1020
aaggagttca atgcaaggtc aacaacaaa gacctcccat cacccatcga gaaaccatc 1080
tcaaaaatta aagggctagt cagagctcca caagtataca tcttgccgcc accagcagag 1140
cagttgtcca ggaaagatgt cagtctcact gcctgtcta tgggcttcaa ccctgcgac 1200
atcagtgtgg agtggaccag caatgggcat acagaggaga actacaagga caccgcacca 1260
gtcctggact ctgacggttc ttacttcata tacagcaagc tcgatataaa aacaagcaag 1320
tgggagaaaa cagattcctt ctcatgcaac gtgagcacg agggtctgaa aaattactac 1380
ctgaagaaga ccatctcccg gtctccgggt aaatga                          1416
```

| | | | |
|---|---|---|---|
| SEQ ID NO: 27 | moltype = AA length = 471 | | |
| FEATURE | Location/Qualifiers | | |
| source | 1..471 | | |
| | mol_type = protein | | |
| | organism = synthetic construct | | |

SEQUENCE: 27

```
MGWLWNLLFL MAAAQSAQAQ IQLVQSGPEL KKPGETVKIS CKASGYTFTT YGMTWVKQAP   60
GKGLKWMGWI NTYSGVPTYA DDFKGRFAFS LETSASTAYL QINNLKNEDT ATYFCARGGR  120
GFAYWGQGTL VTVSAAKTTP PSVYPLAPGC GDTTGSSVTL GCLVKGYFPE SVTVTWNSGS  180
LSSSVHTFPA LLQSGLYTMS SSVTVPSSTW PSQTVTCSVA HPASSTTVDK KLEPSGPIST  240
INPCPPCKEC HKCPAPNLEG GPSVFIFPPN IKDVLMISLT PKVTCVVVDV SEDDPDVRIS  300
WFVNNVEVHT AQTQTHREDY NSTIRVVSAL PIQHQDWMSG KEFKCKVNNK DLPSPIERTI  360
SKIKGLVRAP QVYILPPPAE QLSRKDVSLT CLVVGFNPGD ISVEWTSNGH TEENYKDTAP  420
VLDSDGSYFI YSKLDIKTSK WEKTDSFSCN VRHEGLKNYY LKKTISRSPG K           471
```

| | | | |
|---|---|---|---|
| SEQ ID NO: 28 | moltype = AA length = 452 | | |
| FEATURE | Location/Qualifiers | | |
| source | 1..452 | | |
| | mol_type = protein | | |
| | organism = synthetic construct | | |

SEQUENCE: 28

```
QIQLVQSGPE LKKPGETVKI SCKASGYTFT TYGMTWVKQA PGKGLKWMGW INTYSGVPTY   60
ADDFKGRFAF SLETSASTAY LQINNLKNED TATYFCARGG RGFAYWGQGT LVTVSAAKTT  120
PPSVYPLAPG CGDTTGSSVT LGCLVKGYFP ESVTVTWNSG SLSSSVHTFP ALLQSGLYTM  180
SSSVTVPSST WPSQTVTCSV AHPASSTTVD KKLEPSGPIS TINPCPPCKE CHKCPAPNLE  240
GGPSVFIFPP NIKDVLMISL TPKVTCVVVD VSEDDPDVRI SWFVNNVEVH TAQTQTHRED  300
YNSTIRVVSA LPIQHQDWMS GKEFKCKVNN KDLPSPIERT ISKIKGLVRA PQVYILPPPA  360
EQLSRKDVSL TCLVVGFNPG DISVEWTSNG HTEENYKDTA PVLDSDGSYF IYSKLDIKTS  420
KWEKTDSFSC NVRHEGLKNY YLKKTISRSP GK                                452
```

| | | | |
|---|---|---|---|
| SEQ ID NO: 29 | moltype = AA length = 5 | | |
| FEATURE | Location/Qualifiers | | |
| source | 1..5 | | |
| | mol_type = protein | | |
| | organism = synthetic construct | | |

SEQUENCE: 29

```
TYGMT                                                                5
```

| | | | |
|---|---|---|---|
| SEQ ID NO: 30 | moltype = AA length = 17 | | |
| FEATURE | Location/Qualifiers | | |
| source | 1..17 | | |
| | mol_type = protein | | |
| | organism = synthetic construct | | |

SEQUENCE: 30

```
WINTYSGVPT YADDFKG                                                  17
```

| | | | |
|---|---|---|---|
| SEQ ID NO: 31 | moltype = AA length = 7 | | |
| FEATURE | Location/Qualifiers | | |

```
source                  1..7
                        mol_type = protein
                        organism = synthetic construct
SEQUENCE: 31
GGRGFAY                                                                7

SEQ ID NO: 32           moltype = DNA   length = 705
FEATURE                 Location/Qualifiers
source                  1..705
                        mol_type = other DNA
                        organism = synthetic construct
SEQUENCE: 32
atggtatcca cacctcagtt ccttgtattt ttgcttttct ggattccagc ctccagaggt    60
gacatcttgc tgactcagtc tccagccatc ctgtctgtga gtccaggaga aagagtcagt   120
ttctcctgca gggccagtca gagcattggc acaagcatac actggtatca gcaaagaaca   180
aatggttctc caaggcttct cataaagtat gcttctgagt ctatctctgg gatcccttcc   240
aggtttagtg gcagtggatc aggacagat tttactctta gcatcaacag tgtggagtcc   300
gaagatattg cagattatta ctgtcaacaa agtaatagct ggccgtacac gttcggaggg   360
gggaccaagc tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag cacccctacg   600
ttgaccaagg acgagtatga acgacataac agctatacct gtgaggccac tcacaagaca   660
tcaacttcac ccattgtcaa gagcttcaac aggaatgagt gttag                    705

SEQ ID NO: 33           moltype = AA   length = 234
FEATURE                 Location/Qualifiers
source                  1..234
                        mol_type = protein
                        organism = synthetic construct
SEQUENCE: 33
MVSTPQFLVF LLFWIPASRG DILLTQSPAI LSVSPGERVS FSCRASQSIG TSIHWYQQRT    60
NGSPRLLIKY ASESISGIPS RFSGSGSGTD FTLSINSVES EDIADYYCQQ SNSWPYTFGG   120
GTKLEIKRAD AAPTVSIFPP SSEQLTSGGA SVVCFLNNFY PKDINVKWKI DGSERQNGVL   180
NSWTDQDSKD STYSMSSTLT LTKDEYERHN SYTCEATHKT STSPIVKSFN RNEC         234

SEQ ID NO: 34           moltype = AA   length = 214
FEATURE                 Location/Qualifiers
source                  1..214
                        mol_type = protein
                        organism = synthetic construct
SEQUENCE: 34
DILLTQSPAI LSVSPGERVS FSCRASQSIG TSIHWYQQRT NGSPRLLIKY ASESISGIPS    60
RFSGSGSGTD FTLSINSVES EDIADYYCQQ SNSWPYTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 35           moltype = AA   length = 11
FEATURE                 Location/Qualifiers
source                  1..11
                        mol_type = protein
                        organism = synthetic construct
SEQUENCE: 35
RASQSIGTSI H                                                          11

SEQ ID NO: 36           moltype = AA   length = 7
FEATURE                 Location/Qualifiers
source                  1..7
                        mol_type = protein
                        organism = synthetic construct
SEQUENCE: 36
YASESIS                                                                7

SEQ ID NO: 37           moltype = AA   length = 9
FEATURE                 Location/Qualifiers
source                  1..9
                        mol_type = protein
                        organism = synthetic construct
SEQUENCE: 37
QQSNSWPYT                                                              9

SEQ ID NO: 38           moltype = AA   length = 15
FEATURE                 Location/Qualifiers
source                  1..15
                        mol_type = protein
                        organism = synthetic construct
SEQUENCE: 38
TYLCGAISLA PKAQI                                                      15
```